United States Patent
Starzewski et al.

(10) Patent No.: US 6,184,320 B1
(45) Date of Patent: Feb. 6, 2001

(54) METHOD FOR PRODUCING METALLOCENE COMPOUNDS FORMED BY TWO CARBANIONS

(75) Inventors: Karl-Heinz Aleksander Ostoja Starzewski, Bad Vilbel (DE); Warren Mark Kelly, Airdrie (CA)

(73) Assignee: Bayer Aktiengesellschaft, Leverkusen (DE)

( * ) Notice: Under 35 U.S.C. 154(b), the term of this patent shall be extended for 0 days.

(21) Appl. No.: 09/214,187

(22) PCT Filed: Jul. 2, 1997

(86) PCT No.: PCT/EP97/03463

§ 371 Date: Dec. 30, 1998

§ 102(e) Date: Dec. 30, 1998

(87) PCT Pub. No.: WO98/01455

PCT Pub. Date: Jan. 15, 1998

(30) Foreign Application Priority Data

Jul. 5, 1996 (DE) .............................. 196 27 064

(51) Int. Cl.$^7$ ....................................... C08F 4/44
(52) U.S. Cl. .................... 526/161; 526/160; 526/943; 526/131; 526/352; 526/348.6; 502/152; 556/53; 556/7; 556/20
(58) Field of Search ................... 526/943, 160, 526/170, 133, 172, 131, 161; 556/53, 7, 20

(56) References Cited

U.S. PATENT DOCUMENTS

| | | | |
|---|---|---|---|
| 5,324,800 | 6/1994 | Welborn, Jr. et al. | 526/160 |
| 5,580,939 | 12/1996 | Ewen et al. | 526/127 |
| 5,633,394 | 5/1997 | Welborn, Jr. et al. | 556/11 |
| 5,756,417 | * 5/1998 | De Boer et al. | 502/117 |

FOREIGN PATENT DOCUMENTS

| | | |
|---|---|---|
| 2151558 | 12/1995 | (CA) . |
| 0 638 593 | 2/1995 | (EP) . |
| 0 638 593 A1 | * 2/1995 | (EP) . |
| 0 704 461 | 4/1996 | (EP) . |
| 94/20506 | 9/1994 | (WO) . |

* cited by examiner

Primary Examiner—David W. Wu
Assistant Examiner—R. Harlan

(74) Attorney, Agent, or Firm—Joseph C. Gil; Noland J. Cheung

(57) ABSTRACT

Metallocene compounds of the formula where
- CpI and CpII are carbanions having a cyclopentadienyl-containing structure,
- D is a donor atom and
- A is an acceptor atom, where D and A are linked by a reversible coordinative bond in such a way that the donor group takes on a positive (partial) charge and the acceptor group takes on a negative (partial) charge,
- M represents a transition metal of transition group III, IV, V or VI of the Periodic Table of the Elements (Mendeleev),
- X is one anion equivalent and
- n is, depending on the charge of M, zero, one, two, three or four, are new and can be used as catalysts for the (co) polymerization of olefins, i-olefins, alkines and/or diolefins or for ring-opening polyaddition.

A typical X-ray structure analysis is represented by formula 18a.

18 Claims, No Drawings

METHOD FOR PRODUCING METALLOCENE COMPOUNDS FORMED BY TWO CARBANIONS

FIELD OF THE INVENTION

The present invention relates to metallocene compounds in which a transition metal is complexed by two anionic cyclopentadienyl ligands (carbanions) and the two carbanions are connected to one another by at least one bridge comprising a donor and an acceptor. The coordinative bond formed between the donor atom and the acceptor atom generates a positive (partial) charge on the donor group and a negative (partial) charge on the acceptor group:

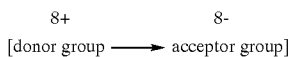

The invention further relates to a process for preparing such new metallocene compounds and to their use as polymerization catalysts.

BACKGROUND OF THE INVENTION

Metallocenes and their use as catalysts in the polymerization of olefins have been known for a long time (EP-A 129 368 and the literature cited therein). Furthermore, EP-A '368 discloses that metallocenes in combination with aluminum alkyl/water as cocatalysts are effective systems for the polymerization of ethylene. (Thus, for example, 1 mol of trimethylaluminum and 1 mol of water form methylaluminoxane=MAO. Other stoichiometric ratios have also been successfully employed (WO 94/20506).) Metallocenes whose cyclopentadienyl frameworks are covalently linked to one another by a bridge are also already known. As an example of the numerous patents and applications in this field, mention may be made of EP-A 704 461 in which the linking group mentioned is a (substituted) methylene or ethylene group, a silylene group, a substituted silylene group, a substituted germylene group or a substituted phosphine group. In EP '461 too, the bridged metallocenes are envisaged as polymerization catalysts for olefins. Despite the numerous patents and applications in this field, there is still a desire for improved catalysts which have a high activity so that the amount of catalyst remaining in the polymer can be made small and which are equally suitable for the polymerization and copolymerization of olefins to give thermoplastics and to give elastomeric products and for the polymerization and copolymerization of diolefins, if desired together with olefins.

SUMMARY OF THE INVENTION

It has now been found that particularly advantageous catalysts can be prepared from bridged metallocene compounds in which the bridge between the two cyclopentadienyl-containing ligands is produced by one, two or three donor-acceptor bonds in each of which a coordinative or dative bond which is, at least formally, superimposed on an ionic bond is formed between the donor atom and the acceptor atom. The reversibility of the donor-acceptor bond permits not only the bridged state denoted by the arrow between D and A but also the unbridged state in which the two x systems can rotate relative to one another, for example by 360°, as a result of their intrinsic rotational energy without the integrity of the metal complex being surrendered. After rotation has occurred, the donor-acceptor bond "snaps" back into place. If a plurality of donors and/or acceptors are present, such "snapping into place" can take place after rotation through less than 360°. Metallocenes of the invention can therefore only be represented by a double arrow and the subformulae (Ia) and (Ib) to encompass both states.

DETAILED DESCRIPTION OF THE INVENTION

The invention accordingly provides metallocene compounds of the formula

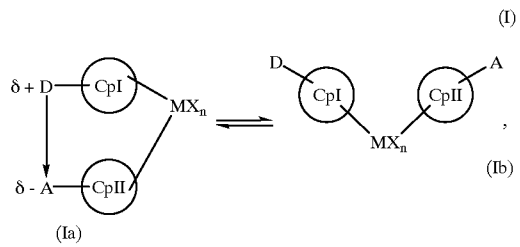

wherein

CpI and CpII are two identical or different carbanions having a cyclopentadienyl-containing structure in which from one to all H atoms can be replaced by identical or different radicals selected from the group consisting of linear or branched $C_1$–$C_{20}$-alkyl which may be monosubstituted to fully substituted by halogen, monosubstituted to trisubstituted by phenyl or monosubstituted to trisubstituted by vinyl; $C_6$–$C_{12}$-aryl; halogenoaryl having from 6 to 12 carbon atoms and organometallic substituents such as silyl, trimethylsilyl and ferrocenyl; and which may be monosubstituted or disubstituted by D and A, D is a donor atom which can additionally bear substituents and which, in its respective bonding state, has at least one free electron pair, A is an acceptor atom which can additionally bear substituents and which, in its respective bonding state, has at least one electron pair vacancy, where D and A are linked by a reversible coordinative bond in such a way that the donor group takes on a positive (partial) charge and the acceptor group takes on a negative (partial) charge, M represents a transition metal of transition group III, IV, V or VI of the Periodic Table of the Elements (Mendeleev) including the lanthanides and actinides, X is one anion equivalent and n is, depending on the charge of M, zero, one, two, three or four.

The invention further provides a process for preparing metallocene compounds of the formula (I), which comprises reacting with one another either one compound each of the formulae (II) and (III)

-continued

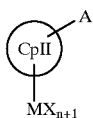
(III)

or one compound each of the formulae (IV) and (V)

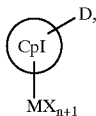
(IV)

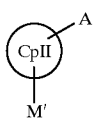
(V)

or one compound each of the formulae (VI) and (VII)

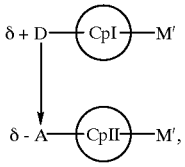
(VI)

$MX_{n+2}$
(VII)

with elimination of M'X in the presence of an aprotic solvent or one compound each of the formulae (VIII) and (III)

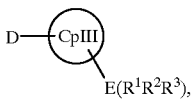
(VIII)

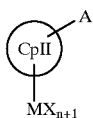
(III)

or one compound each of the formulae (IV) and (IX)

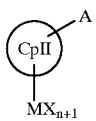
(IV)

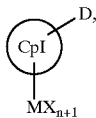
(IX)

or one compound each of the formulae (X) and (VII)

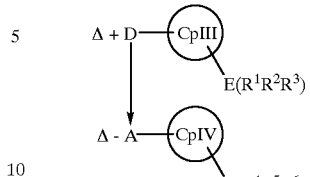
(X)

$MX_{n+2}$
(VII)

with elimination of $E(R^1R^2R^3)X$ and $F(R^4R^5R^6)X$ in the absence or in the presence of an aprotic solvent, where CpI, CpII, D, A, M, X and n are as defined above, CpIII, CpIV are two identical or different uncharged molecule parts having a cyclopentadiene-containing structure, but otherwise the same as CpI and CpII, M' is one cation equivalent of an alkali or alkaline earth metal or Tl, E and F are, independently of one another, one of the elements Si, Ge or Sn and $R^1$, $R^2$, $R^3$, $R^4$, $R^5$ and $R^6$ are, independently of one another, straight-chain or branched $C_1$–$C_{20}$-alkyl, $C_6$–$C_{12}$-aryl, $C_1$–$C_6$-alkyl-$C_6$–$C_{12}$-aryl, $C_6$–$C_{12}$-aryl-$C_1$–$C_6$-alkyl, vinyl, allyl or halogen, where, furthermore, in the formulae (VIII), (IX) and (X) hydrogen can be present in place of $E(R^1R^2R^3)$ and $F(R^4R^5R^6)$ and in this case X can also represent an amide anion of the type $R_2N^\ominus$ or a carbanion of the type $R_3C^\ominus$ or an alkoxide anion of the type $RO^\ominus$, and where it is furthermore possible to react compounds of the formula (II) or (VIII) in the presence of compounds of the formula (V) or (IX) directly with a transition metal compound of the formula (VII). Furthermore, two anions can be connected, with or without insertion of a monoatomic or polyatomic bridge, to form a dianion.

In the reaction of (VIII) with (III) or of (IV) with (IX) or of (X) with (VII) the structure (I) is formed in the last-named variant with elimination of amine $R_2NH$ or $R_2NE(R^1R^2R^3)$ or $R_2NF(R^4R^5R^6)$ or a hydrocarbon compound of the formula $R_3CH$ or $R_3CE(R^1R^2R^3)$ or $R_3CF(R^4R^5R^6)$ or an ether $ROE(R^1R^2R^3)$ or $ROF(R^4R^5R^6)$, where the organic radicals R are identical or different and are, independently of one another, $C_1$–$C_{20}$-alkyl, $C_6$–$C_{12}$-aryl, substituted or unsubstituted allyl, benzyl or hydrogen. Examples of eliminated amine or hydrocarbon, ether, silane, stannane or germane are dimethylamine, diethylamine, di-(n-propyl)-amine, di-(isopropyl)-amine, di-(tert-butyl)-amine, tertiary butylamine, cyclohexylamine, aniline, methyl-phenylamine, di-(allyl)-amine or methane, toluene, trimethylsilylamine, trimethylsilyl ether, tetramethylsilane and the like.

It is also possible to react compounds of the formula (II) or (VIII) directly with a transition metal compound of the formula (VII) in the presence of compounds of the formula (V) or (IX).

The invention further provides for the use of the metallocene compounds described in a process for the homopolymerization or copolymerization of one or more olefins, i-olefins, alkines or diolefins as monomers or for ring-opening polyaddition in the gas, solution, high-pressure or slurry phase at from −60 to +250° C., preferably up to +200° C., and from 0.5 to 5000 bar, preferably from 1 to 3000 bar, and in the presence or absence of saturated or aromatic hydrocarbons or of saturated or aromatic halogenated hydrocarbons and in the presence or absence of water, where these metallocene compounds are used as catalysts in an amount of from $10^1$ to $10^{12}$ mol of all monomers per mol of metallocene and where, furthermore, the reaction can be carried out in the presence of Lewis acids, Bronsted acids or Pearson acids or additionally in the presence of Lewis bases.

Such Lewis acids are, for example, boranes or alanes such aluminum alkyls, aluminum halides, aluminum alkoxides, organoboron compounds, boron halides, boric esters or boron or aluminum compounds which contain both halide substituents and alkyl or aryl or alkoxide substituents, and also mixtures thereof or the triphenylmethyl cation. Particular preference is given to aluminoxanes or mixtures of aluminum-containing Lewis acids with water. According to present day knowledge, all acids act as ionizing agents which form a metallocenium cation whose charge is balanced by a bulky anion which does not coordinate readily.

The invention further provides the reaction products of such ionizing agents with metallocene compounds of the formula (I). They can be described by the formulae (XIa) and (XIb)

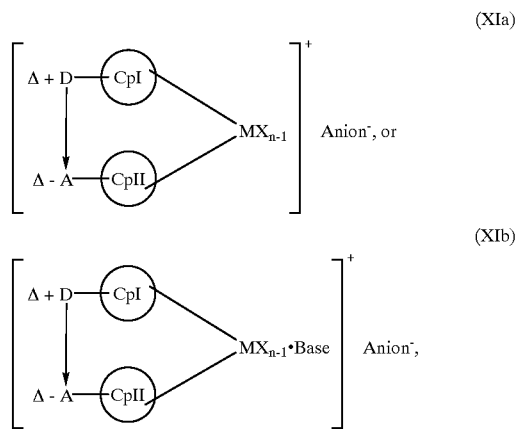

where

Anion represents the overall bulky anion which does not coordinate readily and Base represents a Lewis base.

The novel metallocene compounds of the formula (I) or (XI) can be in monomeric, dimeric or in oligomeric form.

Examples of such anions which do not coordinate readily are

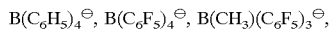

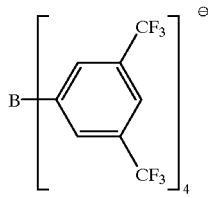

or sulfonates such as tosylate or triflate, tetrafluoroborates, hexafluorophosphates or hexafluoroantimonates, perchlorates and also bulky cluster molecule anions of the carborane type, for example $C_2B_9H_{12}^{\ominus}$ or $CB_{11}H_{12}^{\ominus}$. If such anions are present, metallocene compounds can act as highly active polymerization catalysts even in the absence of aluminoxane. This is especially true when one X ligand is an alkyl group or benzyl. However, it can also be advantageous to use such metallocene complexes having bulky anions in combination with aluminum alkyls such as $(CH_3)_3Al$, $(C_2H_5)_3Al$, $(n-/i-propyl)_3Al$, $(n-/t-butyl)_3Al$, $(i-butyl)_3Al$, the isomeric pentyl-, hexyl- or octyl-aluminum alkyls, or lithium alkyls such as methyllithium, benzyllithium, butyllithium or the corresponding organomagnesium compounds such as Grignard compounds or organozinc compounds. On the one hand, such metal alkyls transfer alkyl groups to the central metal, and on the other hand they trap water or catalyst poisons from the reaction medium or monomers in the polymerization reactions. Examples of boron compounds from which such anions can be derived are:

triethylarnmonium tetraphenylborate,
tripropylammonium tetraphenylborate,
tri(n-butyl)amrnonium tetraphenylborate,
tri(t-butyl)ammonium tetraphenylborate,
N,N-dimethylanilinium tetraphenylborate,
N,N-diethylanilinium tetraphenylborate,
N,N-dimethyl(2,4,6-trimethylanilinium) tetraphenylborate,
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-diethylanilinium tetrakis(pentafluorophenyl)borate,
N,N-dimethyl(2,4,5-trimethylanisinium) tetrakis(pentafluorophenyl)borate,
trimethylammonium tetrakis(2,3,4,6-tetrafluorophenyl) borate,
triethylammonium tetrakis(2,3,4,6-tetrafluorophenyl)borate,
tripropylammonium tetrakis(2,3,4,6-tetrafluorophenyl) borate,
tri(n-butyl)ammonium tetrakis(2,3,4,6-tetrafluorophenyl) borate,
dimethyl(t-butyl)anmuonium tetrakis(2,3,4,6-tetrafluorophenyl)borate,
N,N-dimethylanilinium tetrakis(2,3,4,6-tetrafluorophenyl) borate,
N,N-diethylanilinium tetrakis(2,3,4,6-tetrafluorophenyl) borate,
N,N-dimethyla(2,4,6-nimethylanikinium) tetrakis-(2,3,4,6-tetrafluorophenyl)borate,
dialkylammonium salts such as:
di-(i-propyl)arnmonium tetrakis(pentafluorophenyl)borate and
dicyclohexylammonium tetrakis(pentafluorophenyl)borate,
trisubstituted phosphonium salts such as:
triphenylphosphonium tetrakis(pentafluorophenyl)borate,
tri(o-tolyl)phosphonium tetrakis(pentafluorophenyl)borate,
tri(2,6-dimethylphenyl)phosphonium tetrakis(pentafluorophenyl)borate,
triolylmethyl tetrakis(pentafluorophenyl)borate,
triphenylmethyl tetraphenylborate (trityl tetraphenylborate),
trityl tetrakis(pentafluorophenyl)borate,
silver tetrafluoroborate,
tris(pentafluorophenyl)borane,
tris(trifluoromethyl)borane.

The metallocene compounds of the invention can be isolated as pure materials for use in (co)polymerization. However, it is also possible to generate and use them "in situ" in the (co)polymerization reactor in a manner known to those skilled in the art.

The first and second carbanions CpI and CpII containing a cyclopentadienyl framework can be identical or different. The cyclopentadienyl framework can be, for example, one selected from the group consisting of cyclopentadiene, substituted cyclopentadiene, indene, substituted indene, fluorene and substituted fluorene. There may be from 1 to 4 substituents per cyclopentadiene or fused-on benzene ring. These substituents can be $C_1$–$C_{20}$-alkyl such as methyl, ethyl, propyl, isopropyl, butyl or isobutyl, hexyl, octyl, decyl, dodecyl, hexadecyl, octadecyl or eicosyl, $C_1$–$C_{20}$-alkoxy such as methoxy, ethoxy, propoxy, isopropoxy, butoxy or isobutoxy, hexoxy, octyloxy, decyloxy, dodecyloxy, hexadecyloxy, octadecyloxy or eicosyloxy, halogen such as fluorine, chlorine or bromine, $C_6$–$C_{12}$-aryl such as phenyl, $C_1$–$C_4$-alkylphenyl such as tolyl, ethylphenyl, (i-)propylphenyl, (i-, tert-)butylphenyl or xylyl, halophenyl such as fluorophenyl, chlorophenyl or bromophenyl, naphthyl or biphenylyl, triorganosilyl such as trimethylsilyl (TMS), ferrocenyl and also D or A as defined above. Fused-on aromatic rings can also be partially or fully hydrogenated so that there remains only the double bond which is shared by both the fused-on ring and the cyclopentadiene ring. Furthermore, benzene rings as in indene or fluorene can have one or two further fused-on benzene rings. In addition, the cyclopentadiene or cyclopentadienyl ring and a fused-on benzene ring can together have a further fused-on benzene ring. Such cyclopentadiene frameworks are, in the form of their anions, excellent ligands for transition metals where each cyclopentadienyl carbanion of said substituted or unsubstituted form balancing one positive charge of the central metal in the complex. Specific examples of such carbanions are: cyclopentadienyl, methylcyclopentadienyl, 1,2-dimethyl-cyclopentadienyl, 1,3-dimethyl-cyclopentadienyl, indenyl, phenylindenyl, 1,2-diethyl-cyclopentadienyl, tetramethyl-cyclopentadienyl, ethyl-cyclopentadienyl, n-butyl-cyclopentadienyl, n-octyl-cyclopentadienyl, P-phenylpropyl-cyclopentadienyl, tetrahydroindenyl, propyl-cyclopentadienyl, t-butyl-cyclopentadienyl, benzyl-cyclopentadienyl, diphenylmethyl-cyclopentadienyl, trimethylgermyl-cyclopentadienyl, trimethylstannyl-cyclopentadienyl, trifluoromethyl-cyclopentadienyl, trimethylsilyl-cyclopentadienyl, pentamethyl-cyclopentadienyl, fluorenyl, tetrahydro- or octahydro-fluorenyl, fluorenyls and indenyls which are benzo-fused on the six-membered ring, N,N-dimethylamino-cyclopentadienyl, dimethylphosphino-cyclopentadienyl, methoxy-cyclopentadienyl, dimethylboranyl-cyclopentadienyl, (N,N-dimethylaminomethyl)-cyclopentadienyl.

Apart from the obligatory first donor-acceptor bond between D and A, further donor-acceptor bonds can be formed if additional D and/or A are present as substituents of the respective cyclopentadienesystems. All donor-acceptor bonds have the reversibility described above. For the case of a plurality of D or A, these can take up various positions among those mentioned. The invention accordingly encompasses both the bridged molecular states (Ia) and the unbridged states (Ib). The number of D groups can be identical or different to the number of A groups. Preferably, CpI and CpII are linked via only one donor-acceptor bridge.

Apart from the D/A bridges according to the present invention, covalent bridges can also be present. In this case, the D/A bridges reinforce the stereorigidity and the thermal stability of the catalyst. Changing between a closed and open D/A bond makes possible sequence polymers having higher and lower stereoregularity. In the case of copolymers, such sequences can have different chemical compositions.

Suitable donor groups are, in particular, those in which the donor atom D is an element of main group V, VI or VII of the Periodic Table of the Elements (Mendeleev) and has at least one free electron pair and where, in the case of elements of main group V, the donoratom is present in a bonding state with substituents and in the case of elements of main group VI may be in such a state; donor atoms of main group VII bear no substituents. This is illustrated as follows for the example of phosphorus P, oxygen O and chlorine Cl as donor atoms, where "Subst." represents such substituents mentioned and "-Cp" represents the bond to the cyclopentadienyl-containing carbanion, a line with an arrow is a coordinative bond as defined in formula (I) and other lines represent electron pairs present:

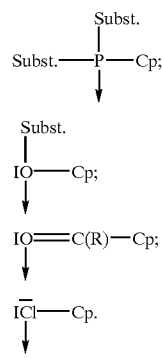

Suitable acceptor groups are, in particular, those whose acceptor atom A is an element of main group III of the Periodic Table of the Elements (Mendeleev), for example boron, aluminum, gallium, indium and thalliumn, which is in a bonding state with substituents and has an electron vacancy.

D and A are linked by a coordinative bond, also known as a dative bond, where D takes on a positive (partial) charge and A takes on a negative (partial) charge.

A distinction is therefore made between the donor atom D and the donor group or between the acceptor atom A and the acceptor group. The coordinative bond D→A is formed between the donor atom D and the acceptor atom A. The donor group is the unit consisting of the donor atom D, any substituents present and the electron pairs present; correspondingly, the acceptor group is the unit consisting of the acceptor atom A, the substituents and the electron vacancy present.

The bond between the donor atom or the acceptor atom and the cyclopentadienyl-containing carbanion can be interrupted by spacer groups in the sense of D-spacer-Cp or A-spacer-Cp. In the third of the above examples of formulae, =C(R)— is such a spacer between O and Cp. Examples of spacer groups are:
dimethylsilyl,
diethylsilyl,
di-n-propylsilyl,
diisopropylsilyl,
di-n-butylsilyl,
di-t-butylsilyl,
di-n-hexylsilyl,
methylphenylsilyl,
ethylmethylsilyl,
diphenylsilyl,
di (p-t-butylphenethylsilyl),
n-hexylmethylsilyl,
cyclopentamethylenesilyl,
cyclotetramethylenesilyl,
cyclotrimethylenesilyl,
dimethylgermanyl, diethylgermanyl,
phenylamino,
t-butylamino,
methylamino,
t-butylphosphino,
ethylphosphino,
phenylphosphino,
methylene,
dimethylmethylene (i-propylidene),
diethylmethylene,
ethylene,
dimethylethylene,
diethylethylene,
dipropylethylene,
propylene,
dimethylpropylene,
diethylpropylene,
1,1-dimethyl-3,3-dimethylpropylene,
tetramethyldisiloxane,
1,1,4,4-tetramethyldisilylethylene,
diphenylmethylene.

Preferably, D and A are bound without a spacer to the cyclopentadienylontainig carbanion. D and A can, independentlyof one another, be located on the cyclopentadiene(yl) ring or a fused-on benzene ring or on another substituent of CpI or CpII. In the case of a plurality of D or A, these can take up various positions among those mentioned.

Substituents on the donor atoms N, P, As, Sb, Bi, O, S, Se or Te and on the acceptor atoms B, Al, Ga, In or Tl are, for example, $C_1–C_{12}$-(cyclo)alkyl such as methyl, ethyl, propyl, i-propyl, cyclopropyl, butyl, i-butyl, tert-butyl, cyclobutyl, pentyl, neopentyl, cyclopentyl, hexyl, cyclohexyl, the isomeric heptyls, octyls, nonyls, decyls, undecyls, dodecyls; the corresponding $C_1–C_{12}$-alkoxy groups; vinyl, butenyl, allyl; $C_6–C_{12}$-aryl such as phenyl, naphthyl or biphenylyl, benzyl, each of which may be substituted by halogen, 1 or 2 $C_1–C_4$-alkyl groups, $C_1–C_4$-alkoxy groups, sulfonate, nitro or halogenoalkyl groups, $C_1–C_6$-alkyl-carboxy, $C_1–C_6$-alkyl-carbonyl or cyano (eg. perfluorophenyl, m,m'-bis (trifluoromethyl)-phenyl, tri($C_1–C_{20}$-alkyl)silyl, tri($C_6–C_{12}$-aryl)silyl and analogous substituents with which those skilled in the art are familiar); analogous aryloxy groups; indenyl; halogen such as F, Cl, Br, and I, 1-thienyl, disubstituted amino such as $(C_1–C_{12}$-alkyl$)_2$amino, diphenylamino, tris-($C_1–C_{12}$-alkyl)-silyl, $NaSO_3$-aryl such as $NaSO_3$-phenyl and $NaSo_3$-tolyl, $C_6H_5$—C≡C—; aliphatic and aromatic $C_1–C_{20}$-silyl whose alkyl substituents can be, in addition to those mentioned above, octyl, decyl, dodecyl, stearyl or eicosyl and whose aryl substituents can be phenyl, tolyl, xylyl, naphthyl or biphenylyl; and those substituted silyl groups which are bound via —$CH_2$— to the donor atom or the acceptor atom, for example $(CH_3)_3SiCH_2$—, $(C_1–C_{12}$-alkyl)(phenyl)amino,$(C_1–C_{12}$-alkyl-naphthyl)-amino,$(C_1–C_{12}$-alkylphenyl),amino, $C_6–C_{12}$-aryloxy containing the abovementioned aryl groups, $C_1–C_8$-perfluoroalkyl, perfluorophenyl. Preferred substituents are: $C_1–C_6$-alkyl, $C_5–C_6$-cycloalkyl, phenyl, tolyl, $C_1–C_6$-alkoxy, $C_6–C_{12}$-aryloxy, vinyl, allyl, benzyl, perfluorophenyl, F, Cl, Br, di-($C_1–C_6$-alkyl)-amino, diphenylamino.

Donor groups are ones in which the free electron pair is localized on N, P, As, Sb, Bi, O, S, Se, Te, F, Cl, Br, I; of these, preference is given to N, P, O, S. Examples of donor groups are: $(CH_3)_3N$—, $(C_2H_5)_2N$—, $(C_3H_7)_2N$—, $(C_4H_9)_2N$—, $(C_6H_5)_2N$—, $(CH_3)_2P$—, $(C_2H_5)_2P$—, $(C_3H_7)_2P$—, $(-C_3H_7)_2P$—, $(C_4H_9)_2P$—, $(t-C_4H_9)P$—, (cyclohexyl)$_2P$—, $(C_6H_5)_2P$—, $(CH_3)(C_6H_5)_2P$—, $(CH_3O)_2P$—, $(C_2H_5O)_2P$—, $(C_6H_5O)_2P$—, $(CH_3$—$C_6H_4O)_2P$—, $((CH_3)_2N)_2P$—, methyl-containing phosphino groups, $CH_3O$—, $CH_3S$—, $C_6H_5S$—, —$C(C_6H_5)$=O, —$C(CH_3)$=O, —$OSi(CH_3)_3$, —$OSi(CH_3)_2$—t-butyl, in each of which N and P each bear a free electron pair and O and S each bear two free electron pairs and where, in the two last-named examples, the doubly bonded oxygen is bound via a spacer group, and also systems such as the pyrrolidone ring where the ring atoms which are different from N likewise act as spacers.

Acceptor groups are ones in which an electron pair vacancy is present on B, Al, Ga, In or Tl, preferably B, Al or Ga; examples are: $(CH_3)_2B$—, $(C_2H_5)_2B$—, $H_2B$—, $(C_6H_5)_2B$—, $(CH_3)(C_6H_5)B$—, (vinyl)$_2B$—, (benzyl)$_2B$—, $Cl_2B$—, $(CH_3O)_2B$—, $Cl_2Al$—, $(CH_3)_2Al$—, $(i-C_4H_9)_2Al$—, $(Cl)(C_2H_5)Al$—, $(CH_3)_2Ga$—, $(C_3H_7)_2Ga$—, $((CH_3)_3Si$—$CH_2)_2Ga$—, (vinyl)$_2Ga$—, $(C_6H)_2Ga$—, $(CH_3)_2In$—, $((CH_3)_3Si$—$CH_2)_2In$—, (cyclopentadienyl)$_2In$—.

Further suitable donor and acceptor groups are those which contain chiral centers or in which 2 substituents form a ring with the D or A atom. Examples of such groups are

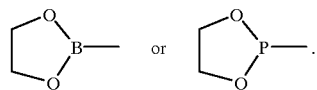

Preferred donor-acceptor bridges between CpI and CpII are, for example, the following:

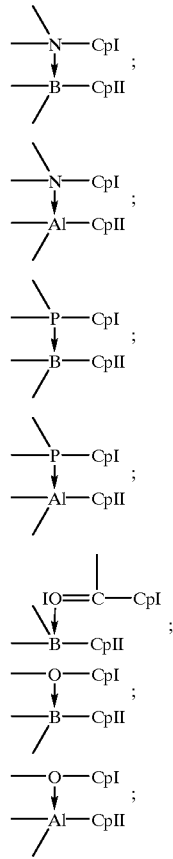

-continued

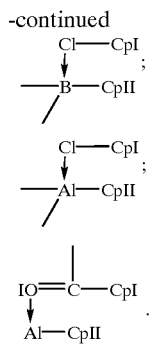

M represents a transition metal from transition group III, IV, V or VI of the Periodic Table of the Elements (Mendeleev), including the lanthanides and actinides; examples which may be mentioned are: Sc, Y, La, Sm, Nd, Lu, Ti, Zr, Hf, Th, V, Nb, Ta, Cr. Preference is given to Ti, Zr, Hf, V, Nb and Ta.

In forming the metallocene structure of the above formula (I), one cyclopentadienyl-containing carbanion balances one positive charge on the transition metal M.

Remaining positive charges on the central atom M are balanced by further, usually monovalent anions X of which two identical or different anions can also be linked to one another (dianions

for example monovalent or divalent negative radicals from identical or different, linear or branched, saturated or unsaturated hydrocarbons, amines, phosphines, thioalcohols, alcohols or phenols. Monovalent anions such as $CR_3^-$, $NR_2^-$, $PR_2^-$, $OR^-$, $SR_2^-$, etc., can be connected by saturated or unsaturated hydrocarbon or silane bridges to form dianions, where the number of bridging atoms can be 0, 1, 2, 3, 4, 5 or 6, preferably from 0 to 4 bridging atoms, particularly preferably 1 or 2 bridging atoms. The bridging atoms can bear, apart from H atoms, further hydrocarbon substituents R. Examples of bridges between the monovalent anions are $-CH_2-$, $-CH_2-CH_2-$, $-(CH_2)_3-$, $CH=CH$, $-(CH=CH)_2-$, $-CH=CH-CH_2-$, $-CH_2-CH=CH-CH_2-$, $-Si(CH_3)_2-$, $C(CH_3)_2-$. Examples of X are: hydride, chloride, methyl, ethyl, phenyl, fluoride, bromide, iodide, the n-propyl radical, the i-propyl radical, the n-butyl radical, the amyl radical, the i-amyl radical, the hexyl radical, the i-butyl radical, the heptyl radical, the octyl radical, the nonyl radical, the decyl radical, the cetyl radical, methoxy, ethoxy, propoxy, butoxy, phenoxy, dimethylamino, diethylamino, methylethylamino, di-t-butylamino, diphenylamino, diphenylphosphino, dicyclohexylphosphino, dimethylphosphino, methylidene, ethylidene, propylidene and the ethylene glycol dianion. Examples of dianions are: 1,4-diphenyl-1,3-butadienediyl, 3-methyl-1,3-pentadienediyl, 1,4-dibenzyl-1,3-butadienediyl, 2,4-hexadienediyl, 1,3-pentadienediyl, 1,4-ditolyl-1,3-butadienediyl, 1,4-bis(trimethylsiyl)-1,3-butadienediyl, 1,3-butadienediyl. Particular preference is given to 1,4-diphenyl-1,3-butadienediyl, 1,3-pentadienediyl, 1,4-dibenzyl-1,3-butadienediyl,2,4-hexadienediyl, 3-methyl-1,3-pentadienediyl, 1,4-ditolyl-1,3-butadienediyl and 1,4-bis(trimethylsilyl)-1,3-butadienediyl. Further examples of dianions are those containing heteroatoms, for instance of the structure

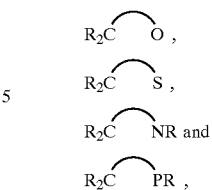

where the bridge is as defined above. Furthermore, particular preference is given, for balancing the charge, to weakly coordinating or non-coordinating anions of the abovementioned type.

Activation by such bulky anions is achieved, for example, by reacting the D/A-metallocenes with tris-(pentafluorophenyl)-borane, triphenylborane, triphenylaluminum, trityl tetrakis-(pentafluorophenyl)-borate or N,N-dialkyl-phenyl-ammonium tetrakis-(pentafluorophenyl)-borate or the corresponding phosphonium or sulfonium salts of borates or alkali metal, alkaline earth metal, thallium or silver salts of borates, carboranes, tosylates, triflates, perfluorocarboxylates such as trifluoroacetate or the corresponding acids. Preference is here given to using D/A-metallocenes whose anion equivalents X=alkyl, aryl or benzyl groups. Such derivatives can also be prepared "in situ" by reacting D/A-metallocenes having other anion equivalents such as X=F, Cl, Br, OR, $NR_2$, etc. beforehand with aluminum alkyls, organolithium compounds or Grignard compounds or zinc or lead alkyls. The reaction products obtainable therefrom can be activated without prior isolation using the abovementioned boranes or borates.

Depending on the charge of M, the index n takes on the value zero, one, two, three or four, preferably zero, one or two. The abovementioned transition metals can, depending inter alia on the groups to which they belong, take on valences/charges of from two to six, preferably from two to four, of which in each case two are balanced by the carbanions of the metallocene compound. Accordingly, in the case of $La^{3+}$ the index n takes on the value one and in the case of $Zr^{4+}$ it takes on the value two; in the case of $Sm^{2+}$, n=zero.

In the process for preparing the metallocene compounds of the formula (I), either one compound each of the above formulae (II) and (III) or one compound each of the above formulae (IV) and (V) or one compound each of the above formulae (VI) and (VII) or one compound each of the above formulae (VIII) and (III) or one compound each of the above formulae (IV) and (IX) or one compound each of the above formulae (X) and (VII) can be reacted with one another with elimination of alkali metal-X, alkaline earth metal-$X_2$, silyl-X, germyl-X, stannyl-X or HX compounds in an aprotic solvent at temperatures of from $-78°$ C. to $+120°$ C., preferably from $-40°$ C. to $+70°$ C., and in a molar ratio of (II):(III) or (IV):(V) or (VI):(VII) or (VIII):(III) or (IV):(IX) or (X):(VII) of 1:0.5–2, preferably 1:0.8–1.2, particularly preferably 1:1. In the cases of the reaction of (VIII) with (III) or (IV) with (IX) or (X) with (VII), it is possible to omit an aprotic solvent if (VIII), (IX) or (X) is liquid under the reaction conditions. Examples of such compounds which may be eliminated are: TlCl, LiCl, LiBr, LiF, LiI, NaCl, NaBr, KCl, KF, $MgCl_2$, $MgBr_2$, $CaCl_2$, $CaF_2$, trimethylchlorosilane, triethylchlorosilane, tri-(n-butyl)-chlorosilane, triphenylchlorosilane, trimethylchlorogermane, trimethylchlorostannane, dimethylamine, diethylamine, dibutylamine and further compounds which can be recognized by those skilled in the art from the abovementioned substitution pattern.

Compounds of the formulae (II) and (IV) are thus carbanions which contain a cyclopentadienyl framework, which contain the 1 to 3 donor groups utilized for the D/A bridging bond in covalently bound form and have a cation as counter ion to the negative charge of the cyclopentadienyl framework. Compounds of the formula (VIII) are uncharged cyclopentadiene frameworks likewise having from 1 to 3 donor groups utilized for the D/A bridging bond, but with leaving groups $E(R^1R^2R^3)$ which can easily be eliminated, eg. silyl, germyl or stannyl groups or hydrogen, in place of the ionic groups.

The second component for forming the metallocene compounds of the invention, namely the compound of the formula (III) or (V) is likewise a carbanion having a cyclopentadienyl framework which is identical to or different from the cyclopentadienyl framework of the compound (II) or (IV), but bears from 1 to 3 acceptor groups utilized for the D/A bridging bond in place of the donor groups. Similarly, compounds of the formula (IX) are uncharged cyclopentadiene frameworks having from 1 to 3 acceptor groups utilized for the D/A bridging bond and leaving groups $F(R^4R^5R^6)$ which can likewise easily be eliminated.

In a completely analogous way, compounds of the formula (VI) or (X) are starting materials having a preformed D→A bond, which are carbanion-counter cation compounds or uncharged cyclopentadiene frameworks which have a total of from 1 to 3 possible D→A bonds and give the metallocene compounds (I) on reaction with compounds of the formula (VII).

Both starting materials of the process of the invention, namely (II) and (III) or (IV) and (V) or (VI) and (VII) or (VIII) and (III) or (IV) and (IX) or (X) and (VII) react spontaneously on being combined with simultaneous formation of the donor-acceptor group —D→A— or the complexation of the metal cation M with elimination of M'X or $E(R^1R^2R^3)X$ or $F(R^4R^5R^6)X$ or HX. In the depiction of the donor-acceptor group, the substituents on D and A have been left out in the interests of clarity.

M' is one cation equivalent of an alkali metal or alkaline earth metal, eg. Li, Na, K, ½ Mg, ½ Ca, ½ Sr, ½ Ba or thallium.

Solvents for the process of the invention are aprotic, polar or nonpolar solvents such as aliphatic and aromatic hydrocarbons or aliphatic and aromatic halogenated hydrocarbons. In principle, it is also possible to use further aprotic solvents which are known to those skilled in the art, but, owing to the simpler work-up, those having excessively high boiling points are less preferred. Typical examples are: n-hexane, cyclohexane, pentane, heptane, petroleum ether, toluene, benzene, chlorobenzene, methylene chloride, diethyl ether, tetrahydroluiran, ethylene glycol dimethyl ether.

The starting materials of the formulae (II), (III), (IV) and (V) for the process of the invention can be prepared by literature methods or by methods similar to these. Thus, for example, using a method similar to that described in J. of Organometallic Chem. (1971), 29, 227, the commercially available trimethylsilyl-cyclopenta diene can be reacted first with butyl-lithium and then with trimethylsilyl chloride to give bis(trimethylsilyl)-cyclopentadiene. This can in turn be reacted with boron trichloride to give trimethylsilyl-cyclopentadienyl-dichloroborane (similar to J. of Organometallic Chem. (1979), 169, 327), which can finally be reacted, using a method similar to that described in J. of Organometallic Chem. (1979), 169, 373, with titanium tetrachloride to give dichloroboryl-cyclopentadienyl-titanium trichloride. This last-named compound already represents a prototype of the compounds of the formula (III); furthermore, the last-named compound can be reacted selectively with trimethylaluminum, with the two chlorine atoms connected to the boron atom being replaced by methyl groups to indicate a further compound of the formula (III). In a manner similar to the process descriptions in J. Am. Chem. Soc. (1983) 105, 3882 and Organometallics (1982) 1, 1591, the commercially available cyclopentadienyl-thallium can be reacted with chloro-diphenylphospine and further with butyl-lithium to give a prototype of compounds of the formula (II).

A further example which may be mentioned is the formation of dimethylstannyl-diphenylphosphino-indene by reaction of indene first with butyl-lithium, as already mentioned above, and subsequently with chlorodiphenylphosphine; the further reaction, first again with butyl-lithium and then with chloro-tributyltin gives the compound mentioned which, after farther reaction with zirconium tetrachloride, gives the diphenylphosphino-indenyl-zirconium trichloride as a representative of compounds of the formula (IV). Such syntheses and methods of preparation are well known to those skilled in the art of organometallic and organoelement chemistry and published in numerous literature publications of which only a few have been mentioned above by way of example.

The metallocene compounds of the invention are very useful as catalysts in processes for the homopolymerization and copolymerization of one or more $C_2$–$C_{40}$-olefins or for the copolymerization of one or more $C_2$–$C_{40}$-olefins with one or more $C_4$–$C_8$-isoolefins, $C_2$–$C_8$-alkines or $C_4$–$C_8$-diolefins in the gas, solution, bulk, high-pressure or slurry phase at from −60 to +250° C. and a pressure of from 0.5 to 5000 bar. The reaction can be carried out in the presence or absence of linear or branched, saturated or aromatic or alkyl-substituted aromatic $C_4$–$C_{20}$-hydrocarbons or of saturated or aromatic halogenated $C_2$–$C_{10}$-hydrocarbons. Such polymerizations can be carried out batchwise or preferably continuously in one or more reactors. In the case of a plurality of reactors or reaction zones, it can be carried out under various polymerization conditions. From $10^1$ to $10^{12}$ mol of (co)monomers are reacted per mol of metallocene compounds. The metallocene compounds of the invention can be used together with cocatalysts. The molar ratio between metallocene compound and cocatalyst is from 1 to 100,000 mol of cocatalyst per mol of metallocene. Cocatalysts are, for example, aluminoxane compounds. These are compounds of the formula

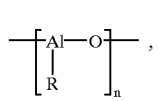

(XII)

where

R represents $C_1$–$C_{20}$-alkyl, $C_6$–$C_{12}$-aryl or benzyl and n is a number from 2 to 50, preferably from 10 to 35.

It is likewise possible to use a mixture of various aluminoxanes or a mixture of their precursors (aluminum alkyls or alkylaluminum halides) in combination with water (in gaseous, liquid, solid or bound form, for instance as water of crystallization). The water can also be added as (residual) moisture of the polymerization medium, the monomers or a support such as silica gel.

The bonds projecting from the square brackets of formula (XI) have R groups or $AlR_2$ groups as end groups of the oligomeric aluminoxane. Such aluminoxanes are generally in the form of a mixture of a plurality of them having different chain lengths. Close examination has also revealed aluminoxanes having a cyclic or cage-like structure. Aluminoxanes are commercially available compounds. In the specific case of R=CH$_3$, the compounds are known as methylaluminoxanes (MAO).

Further cocatalysts are aluminum alkyls, lithium alkyls or organomagnesium compounds such as Grignard compounds or partially hydrolyzed organoboron compounds. Preferred cocatalysts are aluminoxanes.

The activation with the cocatalyst or the generation of the bulky, non-coordinating or weakly coordinating anion can be carried out in the autoclave or in a separate reaction vessel (preactivation). The activation can be carried out in the presence or absence of the monomer(s) to be polymerized. The activation can be carried out in an aliphatic or aromatic or halogenated solvent or suspension medium or on the surface of a catalyst support material.

The metallocene compounds and the aluminoxanes can be used either as such in homogeneous form or individually or together in heterogeneous form on supports. The support material can here be of an inorganic or organic nature, for example silica gel, $Al_2O_3$, $MgCl_2$, NaCl, cellulose derivatives, starch and polymers. Either the metallocene compound or the aluminoxane can be applied first to the support and the other components in each case can be added afterwards. Likewise, the metallocene compound can also be activated in homogeneous or heterogeneous form using the aluminoxane and the activated metallocene compound can then be applied to the support.

Support materials are preferably pretreated thermally and/or chemically in order to set a defined water content or OH group concentration or to keep them as low as possible. A chemical pretreatment can comprise, for example, reacting the support with aluminum alkyl. Before use, inorganic supports are usually heated at from 100° C. to 1000° C. for from 1 to 100 hours. The surface of such inorganic supports, in particular of silica (SiO$_2$), is from 10 to 1000 m$^2$/g, preferably from 100 to 800 m$^2$/g. The particle diameter is from 0.1 to 500 microns ($\mu$), preferably from 10 to 200$\mu$.

Olefins, i-olefins, alkines and diolefins to be homopolymerized or copolymerized are, for example, ethylene, propylene, 1-butene, i-butene, 1-pentene, 1-hexene, 1-octene, 3-methyl-1-butene, 4-methyl-1-pentene, 4-methyl-1-hexene, 1,3-butadiene, isoprene, 1,4-hexadiene, 1,5-hexadiene and 1,6-octadiene, chloroprene, acetylene and methylacetylene. Furthermore a cyclizing polymerization can be carried out with c,co)-diolefins, forming, for example poly-(methylene-1,3-cyclopentane) from 1,5-hexadiene:

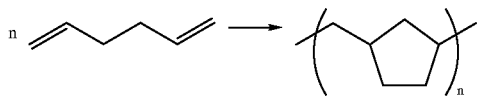

If trialkylsilyl-substituted α,ω)-diolefins are used in this reaction, a functional group can be introduced afterwards by polymer-analogous reaction. Such olefins and diolefins can also be substituted, for example by phenyl, substituted phenyl, halogen, the esterified carboxyl group or the acid anhydride group; compounds of this type are, for example, styrene, methylstyrene, chlorostyrene, fluorostyrene, indene, 4-vinyl-biphenyl, vinyl-fluorene, vinyl-anthracene, methyl methacrylate, ethyl acrylate, vinylsilane, trimethylallylsilane, vinyl chloride, vinylidene chloride, tetrafluoroethylene, isobutylene, vinyl carbazole, vinylpyrrolidone, acrylonitrile, vinyl ethers and vinyl esters. Furthermore, ring-opening polyadditions, for instance of lactones such as ε-caprolactone or δ-valerolactone or of lactams such as c-caprolactam are possible according to the invention. Preferred monomers are: ethylene, propylene, butene, hexene, octene, 1,5-hexadiene, 1,6-octadiene, methyl methacrylate, ε-caprolactone, δ-valerolactone and acetylene. It is possible to carry out said (co)polymerizations in the presence of hydrogen, for instance for regulating the molar mass.

The homopolymerizations or copolymerizations or polyadditions to be carried out using the metallocene compounds of the invention are carried out adiabatically or isothermally in the range of the temperatures and pressure indicated. These are high-pressure processes in autoclaves or tube reactors, solution processes and also polymerization in bulk, processes in the slurry phase in stirred reactors or loop reactors and also processes in the gas phase, with the pressures for the slurry, solution and gas phase not exceeding 65 bar. Such polymerizations can also be carried out in the presence of hydrogen. All these processes have long been known and those skilled in the art are familiar with them. It is now an advantage of the metallocene compounds of the invention that, by means of selection of the substituents, they can be prepared both as soluble metallocene compounds, if desired applied to supports, and as insoluble metallocene compounds. Soluble metallocene compounds are used for the high-pressure process and the solution process; heterogeneous metallocene compounds are used, for example, in the gas phase.

As a result of the donor-acceptor bridge, the metallocene compounds of the invention make it possible for the two cyclopentadienyl frameworks to open to a defined extent like a beak, ensuring not only a high activity but also a high stereoselectivity, a controlled molecular weight distribution and a uniform incorporation of comonomers. A defined beak-like opening also makes room for bulky comonomers. Furthermore, a high uniformity in the molecular weight distribution results from the uniform and defined location of the polymerization occurring by insertion (single site catalyst).

The D/A structure can effect extra stabilization of the catalysts up to high temperatures so that the catalysts can also be used in the high-temperature range from 80 to 250° C., preferably from 80 to 180° C. The possible thermal dissociation of the donor-acceptor bond is reversible and, by means of this self-organization process and self-repairing mechanism, leads to particularly high-value catalyst properties. The thermal dissociation makes possible, for example, a targeted broadening of the molecular weight distribution, giving the polymers better processibility. This effect also occurs, for example, in the case of those catalysts in which CpI and CpII are linked by both a covalent and a D/A bridge. The D/A metallocene structures of the invention make possible, for example, a degree of defect-free polyethylene formation which is not achieved using classical catalysts. Correspondingly, the ethene polymers can have extraordinarily high melting points, for example above 135° C–160° C. (maximum in the DSC curve). Such linear polyethylenes which are obtained directly in the polymerization process and have melting points of from 140 to 160° C. (maxima in the DSC curves), preferably from 142 to 160° C., particularly preferably from 144 to 160° C., are new. Such new high-melting polyethylenes display, for example, improved mechanical properties and heat distortion resistance (sterilizability in medical applications) compared with the known polyethylenes and thereby open up possible applications which have hitherto not appeared possible for polyethylene and, for example, whose requirements could hitherto only be met by high-tacticity polypropylene. Further features are high enthalpies of fusion and high PE molar masses.

Although the polymerization temperature increase lowers the PE molar mass in a wide temperature range, this occurs without appreciable decrease in activity and without going outside the overall range of industrially important high PE molar masses and high PE melting points.

Furthermore, it has been observed that metallocene compounds of the invention having a suitable symmetry effect a regiospecific (isotactic, syndiotactic) polymerization of suitable monomers, but in the upper part of the temperature range mentioned trigger an increasingly nonspecific (atactic) linking of the monomer units of the same monomer. This phenomenon has not yet been fully studied, but could be in agreement with the observation that coordinative bonds which have an ionic bond superimposed on them, like the donor-acceptor bonds in the metallocene compounds of the invention, display increasing reversibility at higher temperature. Thus, for example, in the ethylene-propylene copolymerization it has been observed that for the same supply of the two comonomers, a copolymer having a high propylene contact is formed at a low polymerization temperature while the propylene content decreases with increasing polymerization temperature until finally polymers containing predominantly ethylene are formed at high temperature.

The reversible dissociation and association of the D/A structure and the relative rotation of the Cp frameworks made possible in this way can be schematically shown as follows:

The bonding position between the transition metal M and H or substituted or unsubstituted C, for instance the still bound C of the butadienediyl dianion shown in the example formula, is then the site for the olefin insertion for polymerization.

Furthermore, the π complexes or metallocene compounds to be used according to the invention are suitable for preparing both thermoplastic and elastomeric polymers by the various methods of preparation mentioned above, with it being possible to obtain both highly crystalline polymers having an optimized melting range and amorphous polymers having an optimized glass transition temperature.

EXAMPLES

All reactions were carried out under strictly anaerobic conditions and using Schlenk techniques or the high-vacuum technique. The various solvents were dry and saturated with argon. Chemical shifts δ are given in ppm, relative to the respective standard: $^1$H(tetramethylsilane), $^{13}$C(tetramethylsilane), $^{31}$P (85% strength $H_3PO_4$), $^{11}$B (boron trifluoride etherate 18.1 ppm). Negative signs indicate a shift to higher field.

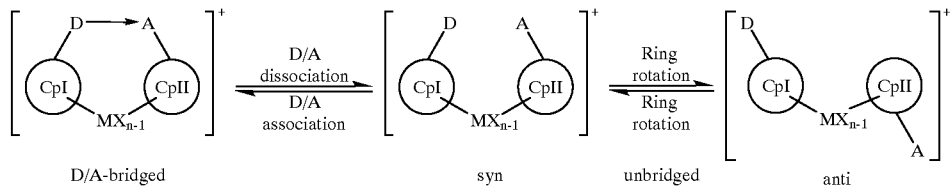

D/A-bridged          syn          unbridged          anti

A further valuable property of the D/A metallocene compounds of the invention is the possibility of self-activation and thus the elimination of the need for expensive cocatalysts, particularly in the case of dianionic

derivatives. Here, the acceptor atom A in the open form of the D/A metallocene compound binds an X ligand, for example one side of a dianion, to form a zwitterionic structure and thus generates a positive charge on the transition metal, while the acceptor atom A takes on a negative charge. Such self-activation can be intramolecular or intermolecular. This may be illustrated by means of the example of the preferred linking of two X ligands to form a chelating ligand, namely the butadienediyl derivative:

Example 1
(Bis-(trimethylsilyl)-cyclopentadiene, Compound 1)

14.7 g (0. 106 mol) of trimethylsilyl-cyclopentadiene (obtained from Fluka) and 150 ml of tetrahydrofuiran (THF) were placed in a reaction flask and cooled to 0° C. 47.4 ml of a solution of butyl-lithium in n-hexane (2.3 molar; total amount: 0.109 mol) were added dropwise to the above mixture over a period of 20 minutes. After addition was complete, the yellow solution was stirred further for one hour; the cooling bath was then removed. At room temperature, the solution was stirred further for one hour and then cooled to −20° C. 14.8 mol (0.117 mol) of trimethylsilyl chloride were then added dropwise over a period of 10 minutes and the reaction mixture was stirred for two hours at −10° C. The cooling bath was then removed and the reaction solution was warmed to room temperature and stirred further for one hour. The reaction mixture was filtered through Celite; the filter was washed with hexane and the

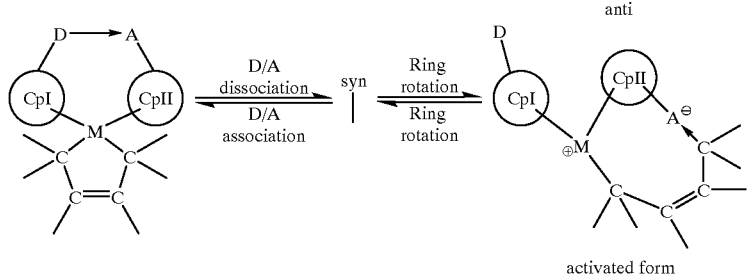

activated form hexane was removed from the combined filtrates under reduced pressure. The crude product was distilled at 26° C. and 0.4 mbar to give 19 g of pure product of Compound 1 (85% of the theoretical yield). Boiling point and NMR data correspond to the literature data (J. Organometallic Chem. 29 (1971), 227; ibid. 30 (1971), C57; J. Am. Chem. Soc. 102 (1980), 4429; J. Gen. Chem. USSR, Eng. Transl. 43 (1973), 1970; J. Chem. Soc., Dalton Trans. 1980, 1156).

$^1$H NMR (400 MHz, $C_6D_6$): δ=6.74 (m, 2H), 6.43 (m, 2H), −0.04 (s, 18H).

Example 2

(Trimethylsilyl-cyclopentadienyl-dichloroborane, Compound 2)

16 g (0.076 mol) of Compound 1 were placed in a round-bottom flask which was provided with a dry ice cooling bath. 8.9 g (0.076 mol) of $BCl_3$ were condensed at −78° C. into a Schlenk tube and then added dropwise to the round-bottom flask over a period of 5 minutes. The reaction mixture was slowly warmed to room temperature over a period of 1 hour and then held at from 55 to 60° C. for a further period of 2 hours. All volatile compounds were removed under reduced pressure (3 mm Hg=4 mbar). Subsequent distillation at 39° C. and 0.012 mbar gave 14.1 g of Compound 2 (85% of the theoretical yield). The $^1$H NMR agrees with the literature data and showed that a series of isomers had been prepared (cf. J. Organometallic Chem. 169 (1979), 327). $^{11}$B NMR (64.2 MHz, $C_6D_6$): δ=+31.5.

Example 3

(Dichloroboranyl-cyclopentadienyl-titanium trichloride, Compound 3)

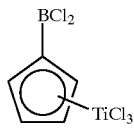

3

11.4 g (0.052 mol) of Compound 2 and 100 ml of methylene chloride ($CH_2Cl_2$) were placed in a 250 ml Schlenk tube. This solution was cooled to −78° C. and 9.8 g (5.6 ml, 0.052 mol) of titanium tetrachloride were added dropwise over a period of 10 minutes. The resulting red solution was slowly warmed to room temperature and stirred further for 3 hours. The solvent was removed under reduced pressure to give a dirty-yellow product. 200 ml of hexane were added to the crude solid and the resulting yellow solution was filtered and cooled overnight in a refrigerator, giving 12.3 g (79% of the theoretical yield) of yellow crystals of Compound 3. Attention may be drawn to the fact that 62% of the theoretical yield was obtained in J. Organometallic Chem. 169 (1979), 373, where the reaction was carried out in a hydrocarbon solvent such as petroleum ether or methylcyclohexane.

$^1$H NMR (400 MHz, $CD_2Cl_2$): δ=7.53 (t, J=2.6 Hz, 2H), 7.22 (t, J=2.6 Hz, 2H). $^{11}$B NMR (64.2 MHz, $CD_2Cl_2$): δ=+33.

Example 4

(Dimethylboranyl-cyclopentadienyl-titanium trichloride, Compound 4)

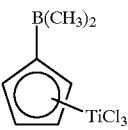

4

In a round-bottom flask, 2.37 g (0.0079 mol) of Compound 3 were dissolved in 100 ml of hexane. This solution was cooled to 0° C. and 4 ml of a 2 molar solution of trimethylaluminum in toluene (0.008 mol) were added dropwise. After addition was complete, the cooling bath was removed and all volatile constituents were removed under reduced pressure. The remaining yellow solid was then dissolved in pentane, solids were filtered off and the clear filtrate was cooled to −78° C., giving 1.5 g (74% of the theoretical yield) of Compound 4. It may be noted that a yield of 87% of the theoretical yield is reported in J. Organometallic Chem. 169 (1979), 373, where tetramethyltin was used as alkylating agent; however, it was not possible to obtain the Compound 4 free of trimethyltin chloride formed.

$^1$H NMR (400 MHz, $CD_2Cl_2$): δ=7.48 (t, J 2.5 Hz, 2H), 7.23 (t, J=2.5 Hz, 2H), 1.17 (s, 6H). $^{11}$B NMR (64.2 MHz, $CD_2Cl_2$): δ=+56.

Example 5

(Diphenylphosphino-cyclopentadienyl-lithium, Compound 6)

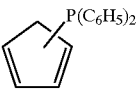

5

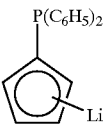

6

50 g (0.186 mol) of cylopentadienyl-thallium (obtained from Fluka) together with 300 ml of diethyl ether were placed in a 500 ml flask. The slurry was cooled to 0° C. and 34.2 ml (0.186 mol) of diphenylchlorophosphine were added dropwise over a period of 10 minutes. The slurry was then warmed to room temperature, stirred for one hour and finally filtered through a frit. The solvent was then taken off under reduced pressure and left 39.5 g (85% of the theoretical yield) of the intermediate diphenylphosphino-cyclopentadiene, Compound 5. 18.6 g (0.074 mol) of Compound 5 were then diluted with toluene and cooled to 0° C. 33.2 ml of a 2.24 molar solution of butyl-lithium in hexane (0.074 mol) were added to the above solution over a period of 10 minutes. After warming to room temperature and stirring for 2 hours, the yellow solution gave a precipitate which was filtered off and washed with toluene and subsequently with hexane. Drying under reduced pressure gave 13.2 g of Compound 6 (70% of the theoretical yield) as a brownish powder (cf. J. Am. Chem. Soc. 105 (1983); 3882; Organometallics 1 (1982), 1591).

$^1$H NMR (400 MHz, d, THF): δ=7.3 (m, 4H), 7.15 (m, 6H), 5.96 (m, 2H), 5.92 (m, 2H), $^{31}$P NMR (161.9 MHz, d. THF): δ=−20.

Example 6

(($(C_6H_5)_2P{\rightarrow}B(CH_3)_2$)-bridged bis-(cyclopentadienyl)-titanium dichloride, Compound 7)

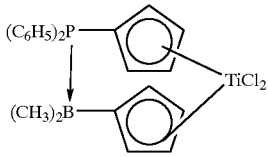

7

0.36 g (0.00139 mol) of Compound 6 and 20 ml of toluene were placed in a round-bottom flask. The resulting solution was cooled to −20° C. and a solution of 0.36 g (0.00139 mol) of Compound 4 in 20 ml of toluene was added dropwise over a period of 20 minutes. After completion of the dropwise addition, the solution was warmed to room temperature over a period of 2 hours and was stirred at this temperature for an additional hour. Insoluble material was removed via a frit and the solvent was distilled off under reduced pressure. The red oily solid was then washed with hexane which was decanted off and the solid was again dried under reduced pressure. This gave 0.28 g (42% of the theoretical yield) of Compound 7 as a red powder.

$^1$H NMR (300 MHz, $CD_2Cl_2$): δ=7.6–7.3 (br, m, 10H), 6.92 (m, 2H), 6.77 (m, 4H), 6.60 (m, 2H), 0.29 (d, $J_{PH}$=19 Hz, 6H); $^{31}$P NMR (161.9 MHz, $CD_2Cl_2$): δ=17.1 (br); $^{11}$B NMR (64.2 MHz, $CD_2Cl_2$): δ=−29 (br).

Example 7

(Tributylstannyl-diphenylphosphino-indene, Compound 8)

10 g (0.086 mol) of indene were placed in a round-bottom flask, diluted with 200 ml of diethyl ether and cooled to −20° C. 36 ml of a 2.36 molar solution of butyl-lithium (0.085 mol) in n-hexane were added to the above solution, with the solution immediately becoming yellow. The cooling bath was removed and the reaction mixture was allowed to warm to room temperature and was stirred further for one hour. The reaction mixture was then cooled again to 0° C. and 19 g (15.9 ml, 0.086 mol) of diphenylchlorophospine were added to form a precipitate. The cooling bath was again removed and the solution was allowed to warn to room temperature while stirring further for one hour. The solution was then again cooled to −20° C. and 36 ml (0.085 mol) of butyl-lithium in n-hexane were added dropwise. After addition was complete, the cooling bath was removed again and the temperature rose to room temperature; the solution was stirred further for 1.5 hours. The slurry was cooled again to 0° C. and 28 g (0.086 mol) of tributyltin chloride were added dropwise. The resulting slurry was warmed to room temperature and stirred further for 1.5 hours, then filtered through a frit and the solvent was removed under reduced pressure. This left 46.9 g of Compound 8 (92% of the theoretical yield) as a heavy yellow oil.

$^1$H NMR (400 MHz, $CDCl_3$): δ=7.5–7.3 (m, 6H), 7.28 (br, s, 6H), 7.14 (pseudo-d t, 7.3 Hz/1.0 Hz, 1H), 7.08 (t, J=7.3 Hz, 1H), 6.5 (br, m, 1H), 4.24 (br, s, 1H), 1.4–1.25 (m, 6H), 1.25–1.15 (m, 6H), 0.82 (t, J=7.2 Hz, 9H), 0.53 (t, J=8 Hz, 6H), $^{31}$P NMR (161.9 MHz, $CDCl_3$): δ=−20.6.

Example 8

(Diphenylphosphino-indenyl-zirconium trichloride, Compound 9)

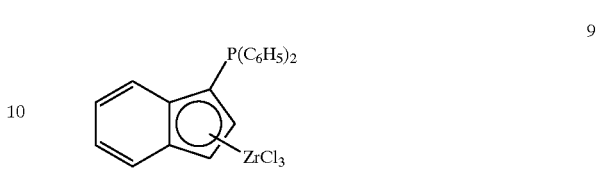

9

A solution of 37 g (0.0628 mol) of Compound 8 in 300 ml of toluene was added over a period of 3 hours to a slurry of 14.6 g of $ZrCl_4$ (99.9% pure, 0.0628 mol, obtained from Aldrich) in 100 ml of toluene at room temperature. The solution immediately became red and slowly changed to orange and finally to yellow. After stirring further for 4 hours, the yellow precipitate was filtered off and washed with toluene and then with hexane. The solid was dried under reduced pressure and gave 15.3 g (50% of the theoretical yield) of Compound 9 as a free-flowing yellow powder. The yield could be readily increased to over 70% if the procedure was carried out at a lower temperature, eg. 30 minutes at −30° C. and 5 hours at 0° C. The product could be further purified by washing out remaining tin compound using pentane in a Soxhlet extractor (extraction time: 8 hours).

Example 9

(($(C_6H_5)_2P{\rightarrow}BCl_2$)-bridged indenyl-cyclopentadienyl-zirconium dichloride, Compound 10)

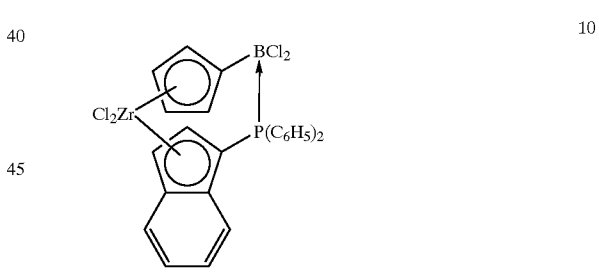

10

4.43 g (0.0089 mol) of the purified Compound 9 and 100 ml of toluene were placed in a Schienk tube. 1.95 g (0.0089 mol) of Compound 2 were added to this slurry. The yellow slurry was stirred at room temperature for 6 hours; during this time, a white precipitate formned. This precipitate (4.1 g, 75% of the theoretical yield) was isolated by filtration and was found to be essentially pure material.

$^1$H NMR (500 MHz, $CD,Cl_2$): δ=7.86 (pseudo ddd, J=8.5/2.5/1 Hz, 1H), 7.75–7.55 (mn, 10H), 7.35 (pseudo ddd, J=8.5/6.9/0.9 Hz, 1H), 7.32 (br t, J=3.1 Hz, 1H), 7.22 (pseudo ddd, J=8.8/6.8/1.1 Hz, 1H), 7.06 (pseudo ddd, J=3.4/3.4/0.8 Hz, 1H), 6.92 (mn, 1H), 6.72 (mn, 1H), 6.70 (br mn, 1H), 6.61 (pseudo q, J=2.3 Hz, 1H), 6.53 (br d, 8.7 Hz, 1H); $^{31}$P NMR (161.9 MHz, $CD_2Cl_2$): δ=6.2 (br, mn); $^{11}$B (64.2 MHz, $CD_2Cl_2$): δ=−18 (br).

Example 10
$((C_6H_5)_2P \rightarrow B(CH_3)_2$-bridged indenyl-cyclopentadienyl-zirconium dichloride, Compound 11)

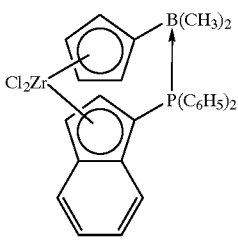

11

50 ml of toluene were added to 1.5 g (0.00247 mol) of Compound 10 from Example 9. The slurry was cooled to 0° C. and 1.2 ml of a 2 molar solution of trimethylaluminum in hexane (0.0024 mol) were added dropwise over a period of 5 minutes. After addition was complete, the cooling bath was removed and the solution was able to warm to room temperature while stirring further for 2 hours. The remaining precipitate was filtered off and the solvent was taken off under reduced pressure, leaving 0.37 g (26% of the theoretical yield) of Compound 11 as a brownish solid.

$^{31}$P NMR (161.9 MHz, $CD_2Cl_2$): δ=14.6; $^{11}$B NMR (64.2 MHz, $CD_2Cl_2$): δ=−28.

Example 11
(Trimethylsilyl-indene, Compound 12)

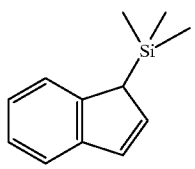

12

25 ml of indene (0.213 mol, distilled from CaH, under reduced pressure) were added to a round-bottom flask which contained 100 ml of THF and had been cooled to 0° C. 94 ml of a 2.3 molar solution of butyl-lithium in hexane (0.216 mol) were added over a period of 20 minutes. After addition was complete, the mixture was stirred for 20 minutes, then warmed to room temperature and stirred further for 30 minutes. After cooling to −20° C., 27.5 ml (0.216 mol) of trimethylchlorosilane were added dropwise, giving a slightly turbid orange solution. After stirring for 1 hour at −10° C. and 1.5 hours at 0° C., the mixture was warmed to room temperature and the solvent was removed under reduced pressure. After again dissolving in hexane, LiCl was filtered off and the hexane was removed under reduced pressure. Distillation of the product (0.045 mbar, 58–60° C.) gave 26.6 g (66% of the theoretical yield) of 12.

$^1$H NMR (400 MHz, $CDCl_3$): δ=7.49 (t, J=7.6 Hz, 1H), 7.28 (ddd, J=7.3/7.2/1 Hz, 1H), 7.21 (ddd, J=7.3/7.2/1.1 Hz, 1H), 6.96 (dd, J=5.6/1.2 Hz, 1H), 6.69 (dd, J=5.3/1.8 Hz, 1H), 3.56 (s, 1H), 0.0 (s, 9H).

Example 12
(Bis-(trimethylsilyl)-indene, Compound 13)

25.4 g (0.135 mol) of Compound 12 were added to a round-bottom flask which contained 100 ml of THF and had been cooled to 0° C. 59 ml of a 2.3 molar solution of butyl-lithium in hexane (0.136 mol) were added over a period of 20 minutes. After addition was complete, the mixture was stirred for 20 minutes and then warmed to room temperature. After stirring for 30 minutes, it was cooled to −20° C. and 17.3 ml of trimethylchlorosilane (0.136 mol) were added dropwise, giving a slightly turbid orange solution. The mixture was stirred for 1 hour at 0° C. and I hour at room temperature and the solvent was then removed under reduced pressure. After redissolving in hexane, LiCl was filtered off and the hexane was removed under reduced pressure. This gave 32 g (90% of the theoretical yield) of 13 as an oil; cf. J. Organometal. Chem. 23 (1970), 407; where hexane was used in place of THF.

$^1$H NMR (400 MHz, $CDCl_3$): δ=7.62 (d, J=7.6 Hz, 1H), 7.52 (d, J=7.5 Hz, 1H), 7.23 (ddd, J=7.35/7.3/0.9 Hz, 1H), 6.9 (d, J=1.7 Hz, 1H), 3.67 (d, J=1.6 Hz, 1H), 0.38 (s, 9H), 0.0 (s, 9H).

Example 13
(Trimethylsilyl-chloroboranyl-indene, Compound 14)

In a similar way to the preparation of Compound 2, 12.3 g (0.047 mol) of Compound 13 were placed in a round-bottom flask which had been cooled to −30° C. and was fitted with a reflux condenser cooled with dry ice. 5.6 g (0.046 mol) of $BCl_3$ were added thereto. After addition was complete, the cooling bath was removed and the reaction mixture warmed to room temperature and was stirred for 3 hours. The temperature was then increased to 55° C. for 6 hours. After cooling and removing the volatile constituents under reduced pressure, the crude product was obtained. Distillation under a high vacuum gave the purified product whose main isomer was identified as follows:

$^1$H NMR (200 MHz, $CDCl_3$): δ=8.3 (d, J=7 Hz, 1H), 8.1 (d, J=1.8 Hz, 1H), 7.5 (dd, J=7.0/1.2 Hz, 1H), 7.4 (m, 3H), 4.0 (d, J=1.8 Hz, 1H), 0.1 (s, 9H); NlB (64.2 MHz, $CD_2Cl_2$): δ=38 (br).

Example 14
$((C_6H_5)_2P \rightarrow BCl_2$-bridged bis-(indenyl)-zirconium dichloride, Compound 15)

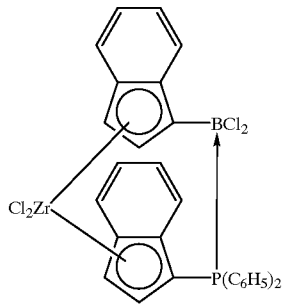

meso-15

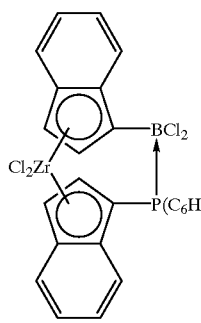

rac-15

4.5 g of Compound 14 (0.017 mol) were added to a slurry of 8.3 g of Compound 9 (0.017 mol) in 200 ml of toluene; the mixture was warmed to 50° C. and stirred for 5 hours. After cooling and filtration, 200 ml of hexane were added, whereupon a precipitate separated from the clear yellow solution. This precipitate was filtered off and dried under reduced pressure. The product was identified as the meso isomer of 15 on the basis of X-ray analysis. The PUB bond length of the bridge was determined as 2.01 Å. Concentration of the toluene/hexane solution to about 10 ml and further addition of 200 ml of hexane gave a second precipitate which was identified as the racemic isomer of 15.

Example 15
(N,N-Dimethyl-O-(methylsulfonyl)-hydroxylamine, Compound 16)

16

9.0 g of N,N-dimethyl-O-hydroxylamine hydrochloride (0.092 mol) were suspended in 70 ml of $CH_2Cl_2$ containing 20 g of triethylamine (0.2 mol) and the suspension was cooled to $-10°$ C. 9.5 g of methylsulfonyl chloride (0.083 mol), dissolved in 70 ml of $CH_2Cl_2$, were slowly added dropwise to the cooled suspension. After addition was complete, the mixture was stirred fituther for 1 hour. Ice water was then added to the reaction mixture and the organic phase was separated off. The remaining water was washed with ether. Washing ether and the $CH_2Cl_2$ fraction were combined, dried over $Na_2SO_4$ and the solvents were removed under reduced pressure at $-10°$ C. This left 5.9 g (46% of the theoretical yield) of Compound 16 as an oil which was stored at $-20°$ C.; cf. Angew. Chem., Int. Ed. Engl. 17 (1978), 687.

$^1$H NMR (400 MHz, $CDCl_3$): $\delta$=3.03 (s, 3H), 2.84 (s, 6H).

Example 16
(N,N-Dimethylamino-cyclopentadienyl-lithium, Compound 17)

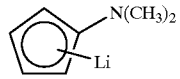

17

A solution of 3 g of cyclopentadienyl-lithium (0.042 mol) in 30 ml of THF was slowly added at $-30°$ C. to a solution of 5.9 g of Compound 16 (0.042 mol) in 20 ml of THF. The mixture was then warmed to $-20°$ C. and stirred for 30 minutes. Hexane was then added and the solution was filtered. 1.8 ml of a 2.3 molar solution of butyl-lithium (0.042 mol) in hexane were then added at $-20°$ C., giving a precipitate. The precipitate was filtered off and washed twice with 20 ml each time of hexane. Drying under reduced pressure gave 2.0 g (40% of the theoretical yield) of Compound 17 as a white powder; cf. Angew. Chem., Int. Ed. Engl. 19 (1980), 1010.

$^1$H NMR (400 MHz, THF): $\delta$=5.34 (br d, J=2.2 Hz, 2H), 5.15 (br d, J=2.2 Hz, 2H), 2.56 (s, 6H).

Example 17
$((CH_3)_2N-+B(CH_3)_2$-bridged bis-(cyclopentadienyl)-titanium dichloride, Compound 18)

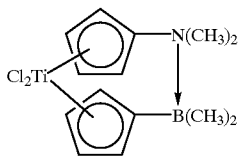

18

A solution of 0.18 g of Compound 4 (0.7 mmol) in 10 ml of toluene was added at $-20°$ C. to a suspension of 0.081 g of Compound 17 (0.7 rnmol) in 10 ml of toluene over a period of 10 minutes, giving a deep red solution. After warming to room temperature over a period of 2 hours, the solution was filtered and the solvent was removed under reduced pressure. After redissolving the resulting red powder in 10 ml of warm toluene and filtering off insoluble material, the solution was stored overnight in a refrigerator, forming 0.1 g (43% of the theoretical yield) of 18 as red needles.

$^1$H NMR (400 MHz, $CD_2Cl_2$): $\delta$=6.85 (t, J=2.3 Hz, 2H), 6.15 (t, J=2.3 Hz, 2H), 6.1 (t, J=2.8 Hz, 2H), 5.57 (t, J=2.8 Hz, 2H), 1.98 (s, 6H), 0.35 (s, 6H); $^{11}$B NMR (64.2 MHz, $CD_2Cl_2$): $\delta$=2.8 (br).

The formula 18a shows the result of the X-ray structural analysis.

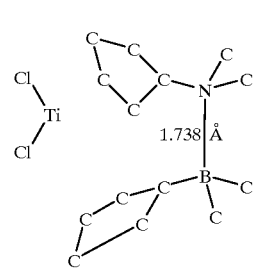

18a

Example 18
(Tributylstannyl-diisopropylphosphino-indene, Compound 19)

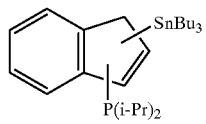

19

100 ml of ether were added to a round-bottom flask containing 3.8 g (0.033 mol) of indene and the mixture was cooled to $-20°$ C. 14.4 ml of a 2.3 molar solution of butyl-lithium in hexane (0.033 mol) were added to the above solution over a period of 5 minutes, giving a yellow solution. After removing the cooling bath, the solution was warmed to room temperature and stirred further for 1.5 hours. The reaction mixture was then cooled to 0° C. and 5.0 g of chlorodiisopropylphosphine (0.033 mol) were added, giving a precipitate. After removing the cooling bath, the solution was warmed to room temperature and stirred for 1 hour. The solution was then cooled to $-20°$ C. and 14.4 ml of a 2.3 molar solution of butyl-lithium in hexane (0.033 mol) were added dropwise. After addition was complete, the cooling bath was removed, the solution was slowly warmed to room temperature and was stirred further for 1.5 hours. After cooling the slurry to 0° C., 10.1 g of chlorotributyltin (0.031 mol) were added dropwise. The resulting slurry was warmed to room temperature and stirred for 1.5 hours. The ether was removed under reduced pressure and the crude product was again dissolved in hexane, filtered and the filtrate was evaporated under reduced pressure, leaving 16.6 g of Compound 19 (yield: 97%) as a heavy yellow oil. Two isomers were obtained in a ratio of 1.5:1. The main isomer was identified as follows: $^1$H NMR (400 MHz, $CD_2Cl_2$): $\delta$=7.71 (d, J=7.2 Hz, 1H), 7.41 (d, J=7.3 Hz, 1H), 7.13 (m, 2H), 6.96 (m, 1H), 4.28 (s with Sn satellites, 1H), 2.21 (m, 1H), 1.54 (m, 1H), 1.45–0.65 (m, 39H). $^{31}$P NMR (161.9 MHz, $CD_2Cl_2$): $\delta$=-11.3 ppm. The secondary isomer was identified as follows: $^1$H NMR (400 MHz, $CD_2Cl_2$): $\delta$=7.6 (d, J=7.4

Hz, 1H), 7.46 (d, J=7.2 Hz, 1H), 7.26 (t, J=7.5 Hz, 1H), 7.1 (m, 1H), 6.71 (m, 1H), 3.48 (m, 1H), 2.21 (m, 1H), 1.54 (m, 1l), 1.45–0.65 (m, 39H). $^{31}$P NMR (161.9 MHz, CD$_2$Cl$_2$): δ–11.5 ppm.

Example 19

(Diisopropylphosphino-indenyl-zirconium trichloride, Compound 20)

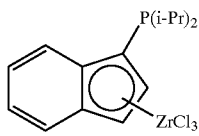

20

A solution of 15.0 g of Compound 19 (0.029 mol) in 50 ml of toluene was added at –78° C. to a slurry of 6.7 g (0.029 mol) of 99.9%-pure ZrCl$_4$ in 300 ml of toluene. After addition was complete, the reaction mixture was stirred for 0.5 hour at –30° C. and subsequently for 4 hours at 0° C. The resulting yellow precipitate was filtered off and washed with toluene and hexane. The solids were dried under reduced pressure, leaving 8.8 g of Compound 20 (yield: 71%) as a free-flowing yellow powder. The powder was further purified by removal of the remaining tin compounds by extraction in a Soxhlet extractor with refluxing toluene for a period of 3 hours at 30 mm Hg and then with pentane for a period of 2 hours. Owing to the insolubility of the compound formed, no $^1$H NMR was obtained.

Example 20

(Diisopropylphosphino-dichloroboranyl-bridgedndenyl-cyclopentadienyl-zirconium dichloride, Compound 21)

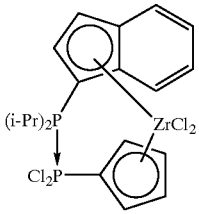

21

0.52 g (0.0012 mol) of Compound 20 and 30 ml of toluene were placed in a Schlenk tube. 0.27 g (0.0012 mol) of Compound 2 was added to this slurry over a period of 5 minutes. The yellow slurry was stirred for 3 hours at room temperature, leaving a slightly turbid solution. The precipitate was removed by filtration, leaving a pale yellow toluene solution. Removing the toluene under reduced pressure left the product as a whitish solid in an amount of 0.47 g (yield: 87%). $^1$H NMR (400 MHz, CD$_2$Cl$_2$): δ=7.84 (pseudo dd, J=8.5, 0.8 Hz, 1H), 7.73 (d, J=8.8 Hz, 1H), 7.5 (pseudo dt, J=7.8, 0.8 Hz, 1H), 7.38 (m, 2H), 6.98 (m, 1H), 6.67 (m, 1H), 6.64 (m, 1H), 6.54 (m, 1H), 6.29 (m, 1H), 3.39 (septet, J=7.1 Hz, 1H), 2.94 (m, 1H), 1.68 (dd, J$_{H-P}$=18.1 Hz, J=7.2 Hz, 3H) 1.64 (dd, J$_{H-P}$=17.4 Hz, J=7.2 Hz, 3H) 1.45 (dd, J$_{H-P}$=15 Hz, J=7.2 Hz, 3H) 1.33 (dd, J$_{H-P}$=14.6 Hz, J=7.3 Hz, 3H). $^{31}$P NMR (161.9 MHz, CD$_2$Cl$_2$): δ–23.1 (br, m); $^{11}$B (80 MHz, CD$_2$Cl$_2$): δ–14.8 (br d, J=110 Hz).

Example 21

(Tributylstannyl-dimethylphosphino-indene, Compound 22)

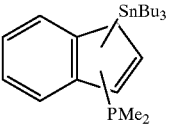

22

150 ml of ether were added to a round-bottom flask containing 5.5 g (0.047 mol) of indene and the mixture was cooled to –20° C. 20.8 ml of a 2.3 molar solution of butyl-lithium in hexane (0.048 mol) were added to the above solution over a period of 5 minutes, giving a yellow solution. After removing the cooling bath, the solution was warmed to room temperature and stirred further for 1 hour. After cooling the reaction mixture to –30° C., 4.6 g of 5.0 g of chlorodimethylphosphine (0.048 mol) in 30 ml of ether were added over a period of 20 minutes, giving a precipitate. After stirring for 2 hours at –20° C., 20.8 ml of a 2.3 molar solution of butyl-lithium in hexane (0.048 mol) were added dropwise. After addition was complete, the cooling bath was removed, the solution was slowly warmed to room temperature and stirred further for 1.5 hours. After cooling the slurry to 0° C., 15.6 g of chlorotributyltin (0.048 mol) were added dropwise. The resulting slurry was warmed to room temperature and stirred for 1.5 hours. The ether was removed under reduced pressure and the crude product was again dissolved in hexane, filtered and the filtrate was evaporated under reduced pressure, leaving 17.4 g of Compound 22 (yield: 78%) as a heavy yellow oil. $^1$H NMR (400 MHz, CD$_2$Cl$_2$): δ 7.67 (d, J=7.5 Hz, 1H), 7.47 (d, J=7.4 Hz, 1H), 7.18 (m, 2H), 6.83 (m, 1H), 4.28 (s with Sn satellites, 1H), 1.43–0.78 (m, 33H). $^{31}$P NMR (161.9 MHz, CD$_2$Cl$_2$): δ–61.6 ppm.

Example 22

(Dimethylphosphino-indenyl-zirconium trichloride, Compound 23)

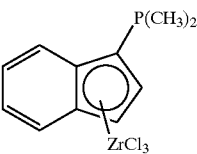

23

A solution of 17.0 g of Compound 22 (0.037 mol) in 50 ml of toluene was added at –78° C. to a slurry of 8.5 g (0.036 mol) of 99.9%-pure ZrCl$_4$ in 200 ml of toluene. After addition was complete the reaction mixture was stirred for 0.5 hour at –30° C. and then for 4 hours at 0° C. The resulting yellow precipitate was filtered off and washed with toluene and hexane. The solids were dried under reduced pressure, leaving 8.3 g of Compound 23 (yield: 61%) as a free-flowing yellow powder. The powder was further purified by removing the remaining tin compounds by extraction in a Soxhlet extractor with refluxing toluene for a period of 3 hours at 30 mm Hg and then with pentane for a period of 2 hours, leaving 7.2 g (yield: 53%) of the product. Owing to the insolubility of this compound, no $^1$H NMR was obtained.

Example 23

(Dimethylphosphino-dichloroboranyl-bridged indenyl-cyclopentadienyl-zirconium dichloride, Compound 24)

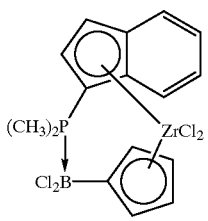

24

30 ml of toluene and 0.55 g of Compound 23 (0.0015 mol) were placed a Schlenk tube. 0.31 g (0.0014 mol) of Compound 2 were added to the above slurry over a period of 5 minutes. The yellow slurry was stirred for 6.5 hours at room temperature, leaving a slightly turbid solution. The precipitate was removed by filtration, leaving a pale yellow toluene solution. After removing the toluene under reduced pressure, the product remained as a whitish solid. After the product had been washed with hexane and dried under reduced pressure, Compound 24 remained as the white solid 0.54 g; yield: 76%). $^1$H NMR (400 MHz, $CD_2Cl_2$): δ 7.84 (pseudo dd, J=7.4 Hz, 1.0 Hz, 1H), 7.60 ((m, 2H), 7.51 (m, 1H), 7.38 (m, 1H), 6.03 (m, 1H), 6.71 (m, 1H), 6.66 (m, 1H), 6.49 (m, 1H), 6.30 (br s, 1H) 2.11 (dd, $J_{H-P}$=11.9 Hz, 3H) 1.94 .(dd, $J_{H-P}$=11.9 Hz, 3H). $^{31}$P NMR (161.9 MHz, $CD_2Cl_2$): δ−5.9 (br, m); $^{11}$B (80 MHz, $CD_2Cl_2$): δ−14.6 (br d, $J_{B-P}$=126 Hz).

Example 24
(2-Methylene, Compound 26)

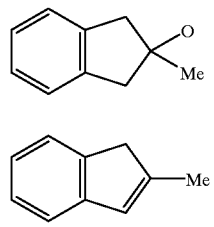

25

26

38.7 g (0.29 mol) of 2-indanone and 300 ml of ether were placed in a round-bottom flask. 96.7 ml of a 3.0 molar solution of $CH_3MgI$ in ether (0.29 mol), which had been diluted with 150 ml of ether, were placed in a second flask. The 2-indanone solution was then added via a hollow needle to the $CH_3MgI$ solution in such amounts that reflux was maintained, giving a precipitate. After addition was complete, the slurry was stirred further for 4 hours under reflux and then cooled to 0° C., after which 100 ml of a saturated solution of $NH_4Cl$ were slowly added. The product was extracted with ether and dried over $MgSO_4$. Removing the solvent under reduced pressure gave 30.1 g (yield: 70%) of 2-methyl-2-indanol (Compound 25) as an oily solid. $^1$H NMR (400 MHz, $CDCl_3$): δ=7.15 (br m, 4H), 3.01 (s, 2H), 2.99 (s, 2H), 1.5 (s, 3H); OH variable.

25.5 g (0.17 mol) of Compound 25, 3.2 g (0.017 mol) of p-toluenesulfonic acid and 500 ml of hexane were placed in a round-bottom flask fitted with a Dean Stark tube. The slurry was refluxed for 3 hours. After cooling, the hexane fraction was decanted from the insoluble products and the solvent was removed under reduced pressure, leaving an oil which was subsequently distilled in a short distillation column at 45° C. and 0.03 mbar, giving 15 g (yield: 68%) of Compound 26. $^1$H NMR (400 MHz, $CDCl_3$): δ 7.33 (d, J=7.6 Hz, 1H), 7.21 (m, 2H), 7.06 (pseudo d t, J=7.2, 1.4 Hz, 1H), 6.45 (br s, 1H), 3.25 (s, 2H), 2.12 (s, 3H).

Reference is made to:
1. Morrison, H.; Giacherio, D. *J. Org. Chem.* 1982, 47, 1058.
2. Ready, T. E.; Chien, J. C. W.; Rausch, M. D. *J. Organom. Chem.* 519, 1966, 21.
3. Wilt, Pawlikowki, Wieczorek, *J. Org. Chem.* 37, 1972, 824.

Example 25
(Tributylstannyl-diisopropylphosphino-2-methylindene, Compound 27)

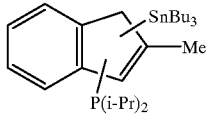

27

150 ml of ether were added to a round-bottom flask containing 5.08 g (0.039 mol) of 2-methylindene 26 and the mixture was cooled to −20° C. 17.0 ml of a 2.3 molar solution of butyl-lithium in hexane (0.039 mol) were added to the above solution over a period of 5 minutes, giving a yellow solution. After removing the cooling bath, the solution was warmed to room temperature and stirred further for 1 hour. The reaction mixture was then cooled to −20° C. and 5.8 g (0.039 mol) of chlorodiisopropylphosphine were added over a period of 5 minutes, giving a precipitate. The cooling bath was then removed and the reaction mixture stirred for 1 hour at room temperature. After cooling to −20° C., 17.0 ml of a 2.3 molar solution of butyl-lithium in hexane (0.039 mol) were added dropwise. After addition was complete, the cooling bath was removed and the solution was slowly warmed to room temperature and stirred further for 1.5 hours. After cooling the slurry to 0° C., 12.4 g (0.038 mol) of chlorotributyltin were added dropwise. The resulting slurry was warmed to room temperature and stirred for 1.5 hours. The ether was removed under reduced pressure and the crude product was again dissolved in hexane, filtered and the filtrate was evaporated under reduced pressure, leaving 20.4 g (yield: 98%) of Compound 27 as a heavy yellow oil. Two isomers were identified by $^{31}$P NMR. $^{31}$P NMR (161.9 MHz, $CD_2Cl_2$): δ−5.9 and −6.6 in a ratio of 2:1.

Example 26
(Diisopropylphosphino-2-methylindenyl-zirconium trichloride, Compound 28)

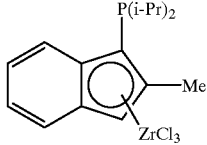

28

A solution of 17.7 (0.033 mol) of Compound 27 in 100 ml of methylene chloride was added at −25° C. to a slurry of 7.7 g (0.033 mol) of $^9$9.9%-pure $ZrCl_4$ in 200 ml of methylene chloride over a period of 10 minutes. After addition was complete, the reaction mixture was slowly warmed to 10° C. over a period of 3 hours, giving a clear, orange solution. After I hour at room temperature, the solvent was removed under reduced pressure and the resulting oil was washed with 2×50 ml of hexane, giving an oily crude product (28) which was used directly for preparing the Compound 29. Owing to the insolubility of this compound no $^1$H NMR was obtained.

Example 27

(Diisopropylphosphino-dichloroboranyl-bridged 2-methylindenyl-cyclopentadienyl-zirconium dichloride, Compound 29)

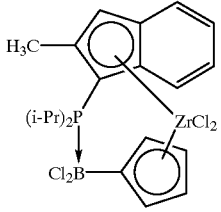

29

5.5 g (0.025 mol) of Compound 2 were added over a period of 5 minutes to a round-bottom flask containing 0.025 mol of the impure Compound 28 in 200 ml of toluene at 0° C. After 1 hour at 0° C., stirring was stopped and the soluble toluene fraction was decanted from the oil formed. After removing the toluene under reduced pressure, 100 ml of hexane were added to the oily solid, giving 7.4 g (yield 54%) of a yellow powder having a purity of about 90%. The product was further purified in a Soxhlet extraction apparatus with refluxing pentane. The final product consisted of a pale yellow powder. $^1$H NMR (400 MHz, CD$_2$Cl$_2$): δ 8.67 (br d, J=7.6 Hz, 1H), 7.71 (m, 1H), 7.35 (m, 2H), 6.62 (br s, 1H), 6.54 (br s, 1H), 6.47 (m, 1H), 6.33 (m, 1H), 6.06 (br s, 1H), 3.3 (br m, 1H), 3.2 (br m, 1H), 2.6 (s, 3H), 2.78 (dd, J=7.1 Hz, J$_{H-P}$=15.3 Hz, 3H) 1.70 (dd, J=7.2 Hz, J$_{H-P}$=15.7 Hz, 3H), 1.57 (dd, J=7.1 Hz, J$_{H-P}$=15.3 Hz, 3H) 1.12 (dd, J=7.1 Hz, J$_{H-P}$=14.0 Hz, 3H). $^{31}$P NMR (161.9 MHz, CD$_2$Cl$_2$): δ 28.4 (br m); $^{11}$B (80 MHz, CD$_2$Cl$_2$) δ–14.3 (br d, JP-B =106 Hz).

Example 28

(Bistrimethylsilyl-(diphenylphosphino)-cyclopentadiene, Compound 30)

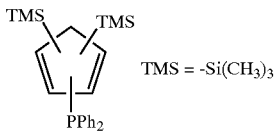

30

TMS = -Si(CH$_3$)$_3$ 76.6 ml of a 2.5 molar solution of butyl-lithium in hexane (0.19 mol) were added at 0° C. to a solution of Compound 1 (40.2 g; 0.19 mol) in 500 ml of ether over a period of 10 minutes. After addition was complete, the bath was removed and the solution was stirred for 1 hour at room temperature. After cooling to 0° C., 42.2 g (0.19 mol) of chlorodiphenylphosphine were added over a period of 10 minutes, after which the bath was removed and the slurry was warmed to room temperature. After stirring for 1 hour at room temperature, the ether was removed under reduced pressure and the product was dissolved again in hexane. After filtering off the salts, the hexane was removed under reduced pressure, leaving 69.1 g (yield: 91%) of Compound 30 as an oil.

$^1$H NMR (400 MHz, CDCl$_3$): δ 7.45 (m, 4H) 7.35 (m, 6H), 6.8 (m, 1H), 6.65 (m, 1H), 6.6 (m, 1H), 0 (s, 18H). $^{31}$P NMR (161.9 MHz, CDCl$_3$): δ–19.5 ppm.

Example 29

(Trimethylsilyl-diphenylphosphino-cyclopentadienyl-zirconium trichloride, Compound 31)

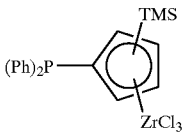

31

A solution of Compound 30 69.1 g (0.175 mol) in 200 ml of methylene chloride was added via a hollow needle to a suspension of 41.5 g (0.178 mol) of 99.9%-pure ZrCl$_4$ in 200 ml of methylene chloride and the mixture was stirred for 8 hours at room temperature. During this time, the solution became turbid. The solids were filtered off, washed with 2×20 ml of toluene and subsequently with 2×20 ml of hexane and dried under reduced pressure. The product consisted of 35 g (yield: 39%) of a pale yellow powder. Owing to the insolubility of the product, no $^1$H NMR was obtained.

Example 30

(Diphenylphosphino-dichloroboranyl-bridged trimethylsilyl-cyclopentadienyl-cyclopentadienyl-zirconium dichloride, Compound 32)

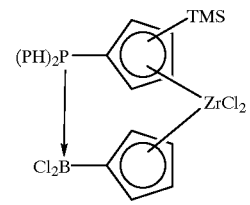

32

A solution of Compound 2 (2.6 g 0.012 mol) was added at 0° C. to a slurry of Compound 31 (5.6 g, 0.011 mol) in 100 ml of toluene. After stirring for 5 hours at 0° C., the yellowish brown solid was removed by filtration, leaving a whitish solution. After removing the toluene under reduced pressure and washing the remaining solid with pentane, the Compound 32 remained as a highly air-sensitive whitish powder (5.5 g; yield: 81%). $^1$H NMR (400 MHz, CD$_2$Cl$_2$): δ 7.8–7.5 (m, 10H), 7.06 (m, 1H), 6.92 (m, 1H), 6.83 (m, 1H), 6.75 (m, 2H), 6.68 (m, 1H), 6.63 (m, 1H), 0.26 (s, 9H). $^{31}$P NMR (161.9 MHz, CD$_2$Cl$_2$): δ 0 (br, m); $^{11}$B (80 MHz, CD$_2$Cl$_2$): δ–16.3 (br d, J$_{B-P}$=82 Hz).

Example 31

(Diisopropylphosphino-cyclopentadienyl-lithium, Compound 33)

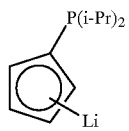

33

50 ml of ether were added to a round-bottom flask containing 1.68 g (0.023 mol) of cyclopentadienyl-lithium. After cooling the reaction flask to –20° C., 3.6 g (0.023 mol) of chlorodiisopropylphosphine were added dropwise. After addition was complete, the cooling bath was warmed to 0° C. and the reaction mixture was stirred for 1 hour. The ether was then removed under reduced pressure and the product was dissolved in toluene and filtered. After rinsing the frit with 2×10 ml of toluene, the reaction mixture was cooled to −20° C. and 9.3 ml of a 2.5 molar solution of butyllithium in hexane (0.023 mol) were added, giving an orange solution. A small fraction was taken for NMR studies and removing the toluene under reduced pressure and washing the resulting oil with hexane gave a pale yellow solid (33). $^1$H NMR (400 MHz, THF): δ=5.89 (m, 2H), 5.83 (br s, 2H), 1.86 (m, 2H), 1.0–0.8 (m, 12H). The main amount was used directly for preparing Compound 34.

Example 32
(Diisopropylphosphino-dimethylboranyl-bridged bis-cyclopentadienyl-titanium dichloride, Compound 34)

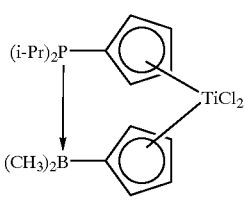

34

A solution of 6.1 g (0.023 mol of Compound 4 in 50 ml of toluene was added at −78° C. to a toluene solution of Compound 33 (0.023 mol) from the mentioned reaction. After stirring for 30 minutes at −78° C., the cooling bath was removed and the solution was stirred further for 2 hours at room temperature. The solids were then removed by filtration and the toluene was removed under reduced pressure. Hexane was subsequently added to the red oily product, giving a red powder which was filtered off, washed with 2×20 ml of hexane and dried under reduced pressure, giving Compound 34 as a red powder (5.95 g, yield based on CpLi: 61%). $^1$H NMR (400 MHz, CD$_2$Cl$_2$): δ=6.96 (m, 2H), 6.94 (pseudo t, J=2.4 Hz 2H), 6.59 (m, 2H), 6.42 (m, 2H), 2.58 (m, 2H), 1.44 (dd, J=7.3 Hz, J$_{H-P}$=14.7 Hz, 6H), 1.27 (dd, J=7.2 Hz, J$_{H-P}$=13.1 Hz, 6H), 0.31 (d, J$_{H-P}$=16.4 Hz, 6H). $^{31}$P NMR (161.9 MHz, CD$_2$Cl$_2$): δ 28.7 (br, m); $^{11}$B (80 MHz, CD$_2$Cl$_2$) δ−29.7 (br m).

Example 33
(Dimethylphosphino-tributylstannyl-2-methylindene, Compound 35)

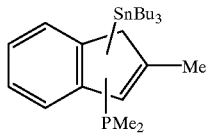

35

100 ml of ether were added to a round-bottom flask containing 6.76 g (0.052 mol) of 2-methylindene (Compound 26) and the mixture was cooled to −20° C. 21 ml of a 2.5 molar solution of butyl-lithium in hexane (0.052 mol) were added to the above solution over a period of 5 minutes, giving a yellow solution. After removing the cooling bath, the solution was warmed to room temperature and stirred further for 1 hour. After cooling the reaction mixture to −20° C., 5.0 g (0.052 mol) of chlorodimethylphosphine were added over a period of 5 minutes, giving a precipitate. The cooling bath was subsequently removed and the reaction mixture was stirred for 1 hour at room temperature. After cooling to −20° C., 21.0 ml of a 2.5 molar solution of butyl-lithium in hexane (0.052 mol) were added dropwise. After addition was complete, the cooling bath was removed and the solution was then slowly warmed to room temperature and was stirred for 1.5 hours. After cooling the slurry to 0° C., 16.9 g (0.052 mol) of chlorotributyltin were added dropwise. The resulting slurry was warmed to room temperature and stirred for 1.5 hours. After removing the ether under reduced pressure, the crude product was dissolved again in hexane, filtered and the filtrate was evaporated under reduced pressure, leaving 24.3 g (yield: 98%) of Compound 35 as a heavy yellow oil. $^{31}$P NMR (161.9 MHz, CD$_2$Cl$_2$): δ−68.5 (s).

Example 34
(Dimethylphosphino-2-methylindenyl-zirconium trichloride, Compound 36)

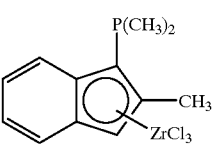

36

A solution of 17.4 g (0.036 mol) of Compound 35 in 100 ml of toluene was added at 0° C. to a slurry of 8.5 g (0.036 mol) of 99.9%-pure ZrCl$_4$ in 100 ml of toluene over a period of 10 minutes. After addition was complete, the reaction mixture was slowly warmed to 10° C. over a period of 1 hour and was then stirred for 6 hours at room temperature. The yellow precipitate was subsequently filtered off, washed with 2×20 ml of toluene and 2×20 ml of hexane and dried under reduced pressure. The powder was further purified by removing the remaining tin compounds by extraction in a Soxhlet extractor with refluxing toluene for a period of 3 hours at 30 mm Hg and then with pentane for a period of 2 hours, leaving 5.8 g (yield: 41%) of Compound 36 as a bright yellow powder. Owing to the insolubility of the compound, no $^1$H NMR was obtained.

Example 35
(Dimethylphosphino-dichloroboranyl-bridged 2-methylindenyl-cyclopentadienyl-zirconium dichloride, Compound 37)

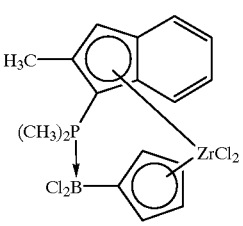

37

2.7 g (0.012 mol) of Compound 2 were added over a period of 5 minutes to a round-bottom flask containing 4.8 g (0.012 mol) of Compound 36 in 125 ml of toluene at room temperature. After stirring for 7 hours, the dark yellow solid was filtered off, washed with 2×20 ml of hexane and dried under reduced pressure, giving 5.5 g (yield: 89%) of Compound 37 as a pale yellow solid. $^1$H NMR (400 MHz, CD$_2$Cl$_2$): δ 8.39 (d, J=8.5 Hz, 1H), 7.71 (m, 1H), 7.4 (m, 2H), 6.64 (m, 2H), 6.46 (pseudo q, J=5.3, 2.9 Hz, 1H), 6.37 (m, 1H), 6.08 (m, 1H), 2.51 (s, 3H), 2.1 (d, J$_{H-P}$=12 Hz, 3H) 2.0 (d, J$_{H-P}$=12 Hz, 3H); $^{31}$P NMR (161.9 MHz, CD$_2$Cl$_2$): δ 5.3 (br, m); SIB (80 MHz, CD$_2$Cl$_2$): δ−14.6 (br d, J$_{B-P}$=116 Hz).

Example 36
(Dicyclohexylboranylcyclopentadienyl-lithium, Compound 39)

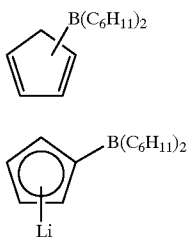

Reference is made to: Herberich, G. E.; Fischer, A. *Organometallics* 1996, 15, 58.

40 ml of a 1 molar solution of chlorodicyclohexylborane in hexane (0.04 mol) were added at −78° C. to 20 ml of cyclopentadienyl-sodium (2M in THF; 0.04 mol) in 100 ml of hexane. After removing the cooling bath, the reaction mixture was warmed to room temperature and stirred for 1 hour. Filtration and removal of the solvent under reduced pressure left 9.1 g (yield 94%) of Compound 38 as a yellow oil which was used directly in the synthesis of Compound 39.

5.3 g (0.038 mol) of 2,2,6,6-tetramethylpiperidine were added to a round-bottom flask containing 40 ml of THF. After cooling to −20° C. and addition of 15 ml of a 2.5 molar solution of butyl-lithium in hexane (0.038 mol), the mixture was stirred for 1 hour at −20° C. and then cooled to −78° C. 9.1 g (0.038 mol) of Compound 38 in 20 ml of hexane were added over a period of 10 minutes to the above solution. The cooling bath was removed and the solution was stirred for 1 hour at room temperature. After removing the solvent under reduced pressure and addition of hexane, the mixture was stirred further for 2 hours, giving a white suspension which was filtered and dried under reduced pressure. This gave 4.6 g (yield: 50%) of Compound 39 as a white powder. $^{11}$B (80 MHz, THF): δ 43.9.

Example 37
(Diphenylphosphino-dicyclohexylboranyl-bridged trimethylsilyl-cyclopentadienyl-cyclopentadienyl-zirconium dichloride, Compound 40)

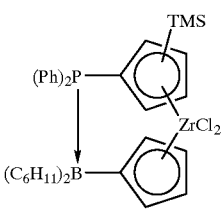

After cooling a Schlenk flask containing 1.4 g (0.0056 mol) of Compound 39 and 2.9 g (0.0056 mol) of Compound 31 to −20° C., 100 ml of toluene were added. After removing the bath, the slurry was stirred for 6 hours at room temperature and subsequently filtered. The solvent was removed under reduced pressure, leaving an oily solid which was washed with hexane and filtered. Drying the solvent under reduced pressure left 1.9 g (yield: 48%) of Compound 40 as a pink solid. $^{1}$H NMR (400 MHz, CD$_2$Cl$_2$): δ 7.6–7.2 (br m, 10H), 7.04 (br s, 1H), 6.95 (m, 1H), 6.82 (m, 1H), 6.76 (br s, 1H), 6.66 (m, 1H), 6.63 (m, 1H), 6.52 (m, 1H) 1.6–1.1 (br m, 22H), 0.26 (s, 9H); $^{31}$P NMR (161.9 MHz, CD$_2$Cl$_2$): δ 16.3; $^{11}$B (80 MHz, CD$_2$Cl$_2$): δ−13.8.

Example 38
(4,7-Dimethylindene, Compound 41)

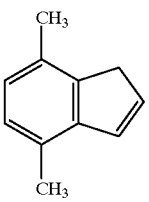

Reference is made to: Erker, G., et al., *Tetrahedron* 1995, 51, 4347.

A 30% strength solution of 153 g (2.8 mol) of sodium methoxide in methanol was diluted with 60 ml of methanol and cooled to 0° C. 34 g (0.52 mol) of cyclopentadiene were added to this solution. After 15 minutes, 39 g (0.34 mol) of 2,5-hexanedione were added dropwise, after which the cooling bath was removed and the reaction mixture was stirred for 2 hours at room temperature. 200 ml of water and 200 ml of ether were subsequently added. The ether layer was removed, washed with water and sodium chloride solution and subsequently dried over Na$_2$SO$_4$. After removing the solvent under reduced pressure and distillation at 65° C. and 0.1 mbar, the Compound 41 remained as an orange oil (40 g; yield: 81%). $^{1}$H NMR (400 MHz, CDCl$_3$): δ 7.35–7.27 (m, 2H), 7.23 (d, J=7.6 Hz, 1H), 6.82 (m, 1H), 3.51 (s, 2H), 2.75 (s, 3H), 2.63 (s, 3H).

Example 39
(Diisopropylphosphino-tributylstannyl-4,7-dimethylindene, Compound 42)

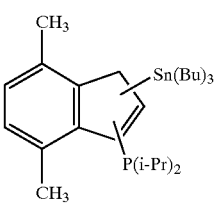

100 ml of ether were added to a round-bottom flask containing 5.0 g (0.035 mol) of 4,7-dimethylindene (Comnound 41) and the mixture was cooled to −20° C. 14 ml of a 2.5 molar solution of butyl-lithium in hexane (0.035 mol) were added over a period of 5 minutes to the above solution, giving a yellow solution. After removing the cooling bath, the solution was warmed to room temperature and stirred further for 1 hour. After cooling the reaction mixture to −20° C., 5.3 g (0.035 mol) of chlorodiisopropylphosphine were added over a period of 5 minutes, giving a precipitate. The cooling bath was then removed and the reaction mixture was stirred for 1 hour at room temperature. After cooling to −20° C., 14.0 ml of a 2.5 molar solution of butyl-lithium in hexane (0.035 mol) were added dropwise. After addition was complete, the cooling bath was removed, the solution was slowly warmed to room temperature and was stirred for 1.5 hours. After cooling the slurry to 0° C., 11.4 g of chlorotributyltin (0.035 mol) were added dropwise. The resulting slurry was warmed to room temperature and stirred for 1.5 hours. The ether was removed under reduced pressure and the crude product was dissolved again in hexane, filtered and the filtrate was evaporated under reduced pressure, leaving 16 g (yield: 83%) of Compound 42 as a heavy yellow oil. $^{31}$P NMR (161.9 MHz, CD$_2$Cl$_2$): δ−9 ppm.

Example 40
(Diisopropylphosphino-4,7-dimethylindenyl-zirconium trichloride, Compound 43)

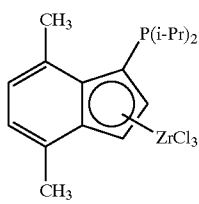

A solution of 16.0 g (0.029 mol) of Compound 42 in $CH_2Cl_2$ (100 ml) was added at −20° C. to a slurry of 6.4 g (0.029 mol) of 99.9%-pure $ZrCl_4$ in 100 ml of $CH_2Cl_2$ over a period of 10 minutes. After addition was complete, the reaction mixture was slowly warmed to room temperature over a period of two hours and was subsequently stirred further for 2 hours at room temperature. The solids were then removed by filtration and the solvent was removed under reduced pressure, leaving the crude Compound 43 as an oil which was used directly for the preparation of Compound 44.

Example 41
(Diisopropylphosphino-dichloroboranyl-bridged 4,7-dimethylindenyl-cyclopentadienyl-zirconium dichloride, Compound 44)

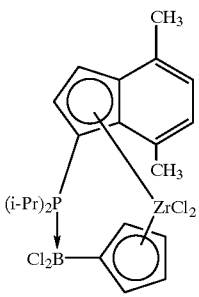

5.0 g (0.023 mol) of Compound 2 were added over a period of 5 minutes to a round-bottom flask containing 10.6 g (0.023 mol) of Compound 43 in 125 ml of toluene at 0° C. After stirring for 1.5 hours at 0° C., the cooling bath was removed and slurry was stirred further for 3 hours at room temperature. The toluene-soluble fraction was then decanted from the heavy oil which had formed during the reaction and was evaporated to dryness under reduced pressure, leaving a heavy oil. After addition of 100 ml of hexane to this oil, the mixture was stirred further and a dark yellow powder was filtered off and was dried under reduced pressure., This procedure left 6.3 g (yield: 48%) of Compound 44 as a dark yellow powder. The product can be further purified by precipitation of a $CH_2Cl_2$ solution of Compound 44 in a hydrocarbon solvent.

$^1$H NMR (400 MHz, $CD_2Cl_2$): δ 8.03 (pseudo t, J=8.5 Hz, 1H), 7.22 (d, J=7 Hz, 1H), 7.08 (d, J=7.1 Hz, 1H), 7.02 (m, 1H), 6.77 (m, 1H), 6.70 (m, 1H), 6.58 (m, 1H), 6.44 (br s, 1H), 3.51 (m, 1H), 2.82 (m, 1H), 2.64 (s, 3H), 2.50 (s, 3H), 1.77 (dd, J=7.2 Hz, $J_{H-P}$=16.3 Hz, 3H), 1.69 (dd, J=7.1 Hz, $J_{H-P}$=15.2 Hz, 3H), 1.58 (dd, J=7.1 Hz, $J_{H-P}$=15.5 Hz, 3H), 1.28 (dd, J=7.2 Hz, $J_{H-P}$=14.5 Hz, 3H); $^{31}$P NMR (161.9 MHz, $CD_2Cl_2$): δ 28.4 (br, m); $^{11}$B (80 MHz, $CD_2Cl_2$): δ−15.3 (d, $J_{P-B}$=107 Hz).

Example 42
(Ethylene polymerization)

50 ml of dry oxygen-free toluene were drawn into a dry, $O_2$-free, magnetically stirred V4A steel autoclave which had been baked out under reduced pressure. The D/A-metallocene catalyst (Compound 10) was preactivated in 15 minutes in toluene at room temperature using MAO (methylaluminoxane, 10% strength in toluene, molar mass 900 g/mol) in an atom (mol) ratio Al/Zr=66.666:1. An aliquot containing $1.5 \times 10^{-7}$ mol of Zr and $1.0 \times 10^{-2}$ mol of Al in 6.8 ml was injected with strict exclusion of air into the autoclave and rinsed in with a further 50 ml of toluene. Polymerization was subsequently carried out for 1 hour at room temperature under a constant ethylene pressure of 10 bar, with the internal temperature rising to 42° C. After venting the autoclave, the reaction mixture was added to 500 ml of ethanol and 50 ml of concentrated aqueous hydrochloric acid and stirred overnight, the polymer was filtered off, washed thoroughly with ethanol and dried to constant weight at 100° C. in a convection drying oven. The PE yield was 2.9 g, corresponding to a catalyst activity of 19.3 metric tons of polymer per mol of Zr and hour. The limiting viscosity η, measured in o-dichlorobenzene at 140° C., was 4.36 dl/g. The DSC measurement gave a melting point of 139° C. and a heat of fusion of 164 J/g.

Example 43
(Ethylene-propylene copolymerization)

50 ml of dry oxygen-free toluene were drawn into a dry, oxygen-free, stirred V4A steel autoclave which had been baked out at 100° C. under reduced pressure. The D/A-metallocene catalyst (Compound 10) was preactivated over a period of 15 minutes in toluene at room temperature using MAO (methylaluminoxane, 10% strength in toluene, molar mass 900 g/mol) in an atom (mol) ratio Al/Zr=50,000:1. An aliquot containing $4 \times 10^{-7}$ mol of Zr and $2 \times 10^{-2}$ mol of Al in 14.7 ml was injected with strict exclusion of air into the autoclave and was rinsed in with a further 50 ml of toluene. Subsequently, 4.3 g of propylene were injected and the autoclave pressure was set to a constant 10 bar using ethylene and polymerization was carried out for 1 hour at 25° C. while stirring. After venting the autoclave, the highly viscous reaction mixture was stirred into a mixture of 500 ml of ethanol and 50 ml of concentrated aqueous hydrochloric acid (37% strength). The suspension of the white polymer precipitated in this way was stirred further for 14 hours, the solid was subsequently isolated by filtration, thoroughly washed with ethanol and dried to constant weight at 100° C. The EPM yield was 3.4 g, corresponding to a catalyst activity of 8.5 metric tons of copolymer per mol of zirconium and hour. A propylene content of 40% by weight was determined by IR spectroscopy. The limiting viscosity η, measured in o-dichlorobenzene at 140° C., was 1.81 dl/g. The DSC measurement gave a glass transition temperature $T_g$=−38° C. and a freezing temperature of −54° C.

Example 44
(Ethylene-propylene copolymerization)

In another copolymerization experiment, the procedure of Example 43 above was repeated. However, the polymerization temperature was 70° C. The amount of D/A-zirconocene (Compound 10) was $4 \times 10^{-7}$ mol at an amount of Al of $1 \times 10^{-2}$ mol. The Al/Zr atom (mol) ratio was 25,000:1. The polymer yield was 5.8 g, corresponding to a catalyst activity of 14.5 metric tons per mol of zirconium and hour. The limiting viscosity Ai, measured in o-dichlorobenzene at 140° C., was 1.10 dl/g. The EP rubber had, according to the DSC measurement, a freezing temperature of −64° C. and a glass transition temperature $T_g$=−60° C.

Examples 45 to 48
(Ethylene polymerization)

In other ethylene polymerization experiments, the procedure of Example 42 was repeated but the D/A-metallocene 7 was used as catalyst and various amounts of MAO were employed. The amount of Ti was $1 \times 10^{-6}$ mol and the autoclave was heated to about 100° C. The Al/Zr ratio was varied between 1250, 2500, 5000 and 10,000. In all 4 experiments, the catalyst activity was from about 3 to 4 metric tons of PE per mol of Ti and hour.

Examples 49 to 52
(Ethylene polymerization)

The procedure of Example 48 was repeated. The amount of Ti (Compound 7) was $1 \times 10^{-6}$ mol, the Al/Zr ratio was 10,000. The autoclave was heated to various temperatures and the polymer properties limiting viscosity 1 and melting point $T_m$ were determined.

T: RT to 60° $\eta$=7.2 dl/g $T_m$=143° C.
T: RT to 80° $\eta$=4.6 dl/g $T_m$=142° C.
T: RT to 100° $\eta$=3.2 dl/g $T_m$=144° C.
T: RT to 120° $\eta$=2.2 dl/g $T_m$=140° C.
(RT=room temperature)

Example 53
(Ethylene polymerization)

The experiment was carried out in a similar way to Example 42, but the D/A-metallocene used as catalyst was the compound meso-15. The amount of Zr was $5 \times 10^{-7}$ mol, the amount of Al was $1 \times 10^{-2}$ mol. After addition of catalyst and ethylene, the autoclave was quickly heated to about 120° C. After a polymerization time of 30 minutes, 4.3 g of polyethylene were isolated, corresponding to an activity of about 17 metric tons of PE per mol of Zr and hour.

The limiting viscosity $\eta$, measured at 140° C. in o-dichlorobenzene, was 1.9 dl/g.

Example 54
(Ethylene polymerization)

The procedure of Example 42 was repeated, but the autoclave was initially charged directly with 100 ml of toluene. The autoclave was heated to 80° C., the catalyst was injected and the ethylene pressure was set to 10 bar. The catalyst used was $1 \times 10^{-6}$ mol of Compound 18 in 2.4 mol of toluene which had been preactivated with $5 \times 10^{-3}$ mol of MAO in 3.3 mol of toluene. The internal temperature rose from 80° C. to 94° C. After 30 minutes, the polymerization was stopped. The PE yield was 3.5 g, corresponding to a catalyst activity of about 7 metric tons of polymer per mol of catalyst and hour. The limiting viscosity $\eta$ was measured in ortho-dichlorobenzene at 140° C. and was 2.95 dl/g. The DSC measurement gave a melting point of 139° C. and a heat of fusion of 165 J/g.

Example 55
(Ethylene polymerization)

The procedure of Example 54 was repeated, but the internal temperature was set to 100° C. The catalyst used was $5 \times 10^{-7}$ mol of Compound 24 in 0.4 mol of chlorobenzene which had been preactivated with $5 \times 10^{-3}$ mol of MAO in 3.3 ml of toluene. The internal temperature rose from 100° C. to 120° C. After polymerization for 30 minutes, 6.2 g of PE had formed, corresponding to a catalyst activity of about 25 metric tons of polymer per mol of catalyst. The limiting viscosity $\eta$, measured in ortho-dichlorobenzene at 140° C., was 1.85 dl/g.

Example 56
(Ethylene polymerization)

The procedure of Example 55 was repeated, but Compound 21 was used as catalyst. In this case, the internal temperature rose from 100° C. to 128° C. The PE yield was 7.9 g after 30 minutes, corresponding to a catalyst activity of about 31.6 metric tons per mol of catalyst and hour. The limiting viscosity $\eta$ in ortho-dichlorobenzene at 140° C. was 1.01 dl/g.

Example 57
(Ethylene polymerization)

The procedure of Example 54 was repeated, but the polymerization was started at 20° C. Metallocene 32 served as catalyst. For this purpose, $2.5 \times 10^{-7}$ mol of catalyst were preactivated with $2.5 \times 10^{-3}$ mol of MAO in toluene. The internal temperature rose from 20° C. to 34° C. After polymerization for 30 minutes, 1.3 g of PE had formed, corresponding to a catalyst activity of about 10.4 metric tons of polymer per mol of catalyst and hour. The limiting viscosity $\eta$ (ortho-dichlorobenzene) was 5.3 dl/g. The DSC measurement gave a melting point of 153° C. in the 1st heating at a rate of 20 K/min. After quenching the sample at 320 K/min, the melting maximum in the 2nd heating was determined as 146° C.

What is claimed is:

1. A metallocene compound of the formula

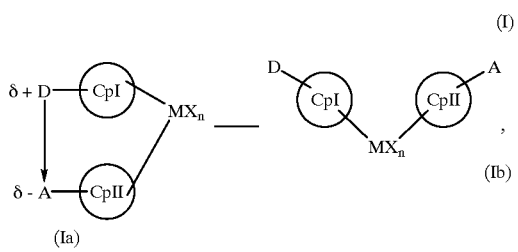

wherein

CpI and CpII are two identical or different carbanions having a cyclopentadienyl-containing structure in which from one to all H atoms can be replaced by identical or different radicals selected from the group consisting of linear or branched $C_1$–$C_{20}$-alkyl which may be monosubstituted to fully substituted by halogen, monosubstituted to trisubstituted by phenyl or monosubstituted to trisubstituted by vinyl; $C_6$–$C_{12}$-aryl; halogenoaryl having from 6 to 12 carbon atoms and organometallic substituents including silyl, trimethylsilyl and ferrocenyl; and which may be monosubstituted or disubstituted by D and A, D is a donor atom which can additionally bear substituents and which, in its respective bonding state, has at least one free electron pair, A is an acceptor atom which can additionally bear substituents and which, in its respective bonding state, has at least one electron pair vacancy, wherein D and A are linked by a reversible coordinative bond in such a way that the donor group takes on a positive charge and the acceptor group takes on a negative charge, M represents a transition metal of transition group III, IV, V or VI of the Periodic Table of the Elements including the lanthanides and actinides, X is one anion equivalent and n is, depending on the charge of M, zero, one, two, three or four.

2. A process for preparing metallocene compounds of the formula

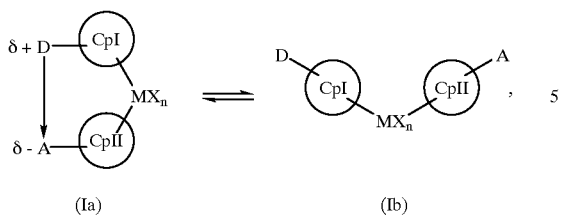

(Ia)                        (Ib)

wherein

CpI and CpII are two identical or different carbanions having a cyclopentadienyl-containing structure in which from one to all H atoms can be replaced by identical or different radicals selected from the group consisting of linear or branched $C_1$–$C_{20}$-alkyl which may be monosubstituted to fully substituted by halogen, monosubstituted to trisubstituted by phenyl or monosubstituted to trisubstituted by vinyl; $C_6$–$C_{12}$-aryl; halogenoaryl having from 6 to 12 carbon atoms; and which may be monosubstituted or disubstituted by D and A, D is a donor atom which can additionally bear substituents and which, in its respective bonding state, has at least one free electron pair, A is an acceptor atom which can additionally bear substituents and which, in its respective bonding state, has at least one electron pair vacancy, wherein D and A are linked by a reversible coordinative bond in such a way that the donor group takes on a positive charge and the acceptor group takes on a negative charge, M represents a transition metal of transition group III, IV, V or VI of the Periodic Table of the Elements including the lanthanides and actinides, X is one anion equivalent and n is, depending on the charge of M, zero, one, two, three or four, which comprises reacting with one another one compound each of the formulae (II) and (III)

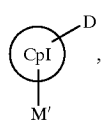
(II)

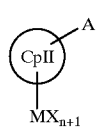
(III)

or one compound each of the formulae (IV) and (V)

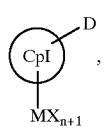
(IV)

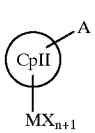
(V)

or one compound each of the formulae (VI) and (VII)

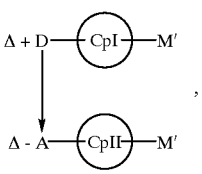
(VI)

$MX_{n+2}$
(VII)

with elimination of M'X in the presence of an aprotic solvent or one compound each of the formulae (VIII) and (III)

(VIII)

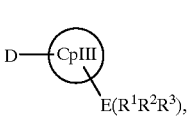
(III)

or one compound each of the formulae (IV) and (IX)

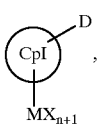
(IV)

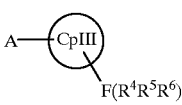
(IX)

or one compound each of the formulae (X) and (VII)

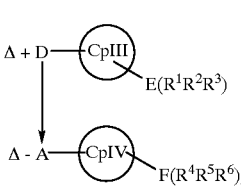
(X)

$MX_{n+2}$
(VII)

with elimination of $E(R^1R^2R^3)X$ and $F(R^4R^5R^6)$ in the absence or in the presence of an aprotic solvent, where CpIII, CpIV are two identical or different uncharged molecule parts having a cyclopentadiene-containing structure, but otherwise the same as CpI and CpII, M' is one cation equivalent of an alkali or alkaline earth metal or Tl, E and F are, independently of one another, one of the elements Si, Ge or Sn and $R^1$, $R^2$, $R^3$, $R^4$, $R^5$ and $R^6$ are, independently of one another, straight-chain or branched $C_1$–$C_{20}$-alkyl, $C_6$–$C_{12}$-aryl, $C_1$–$C_6$-alkyl-$C_6$–$C_{122}$-aryl, $C_6$–$C_{12}$-aryl-$C_1$–$C_6$-alkyl, vinyl, allyl or halogen, where, furthermore, in the formulae (VIII), (IX) and (X) hydrogen can be present in place of $E(R^1R^2R^3)$ and $F(R^1R^2R^3)$ and in this case X can also represent an amide anion of the type $R_2N^\ominus$ or a carbanion of the type $R_3C^\ominus$ or an alkoxide anion of the type $RO^\ominus$, and where it is furthermore possible to react compounds of the formula (II) or (VIII) in the presence of compounds of the formula (V) or (IX) directly with a transition metal compound of the formula (VII).

3. A metallocene compound as claimed in claim 1, wherein the carbanions CpI and CpII are each a cyclopentadienyl framework selected from the group consisting of cyclopentadiene, substituted cyclopentadiene, indene, substituted indene, fluorene and substituted fluorene, in each of which from 1 to 4 substituents selected from the group consisting of $C_1$–$C_{20}$-alkyl, $C_1$–$C_{20}$-alkoxy, halogen, $C_6$–$C_{12}$-aryl, halogenophenyl, D and A are present per cyclopentadiene or fused-on benzene ring, where D and A are as defined in claim 1 and fused-on aromatic rings can be partially or fully hydrogenated.

4. A metallocene compound as claimed in claim 1, wherein the donor atoms D used are elements selected from the group consisting of N, P, As, Sb, Bi, O, S, Se, Te, F, Cl, Br, and I.

5. A metallocene compound as claimed in claim 1, wherein the acceptor atoms A used are elements selected from the group consisting of B, Al, Ga, In, and Tl.

6. A metallocene compound as claimed in claim 1, wherein the donor-acceptor bridges used are selected from the group consisting of

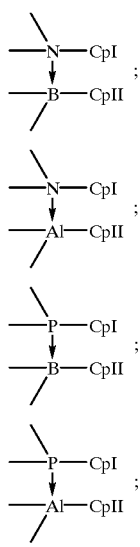

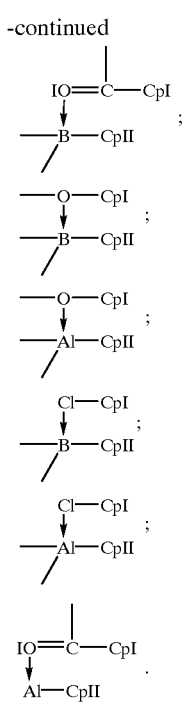

7. A metallocene compound as claimed in claim 1, wherein M represents Sc, Y, La, Nd, Sm, Lu, Ti, Zr, Hf, Th, V, Nb, Ta, or Cr.

8. A metallocene compound as claimed in claim 1, which is used together with a cocatalysts selected from the group consisting of an aluminoxane, a borane and a borate as a catalyst system.

9. A rearrangement product of a metallocene compound of the formula

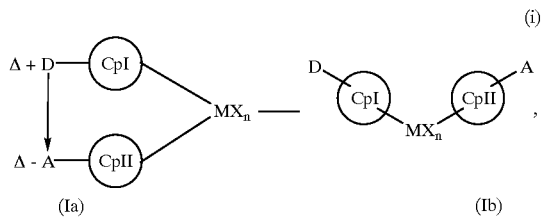

where

CpI and CpII are two identical or different carbanions having a cyclopent-adienyl-containing structure in which from one to all H atoms can be replaced by identical or different radicals selected from the group consisting of linear or branched $C_1$–$C_{20}$-alkyl which may be monosubstituted to fully substituted by halogen, monosubstituted to trisubstituted by phenyl or monosubstituted to trisubstituted by vinyl; $C_6$–$C_{12}$-aryl; halogenoaryl having from 6 to 12 carbon atoms and organometallic substituents such as silyl, trimethylsilyl and ferrocenyl; and which may be monosubstituted or disubstituted by D and A, D is a donor atom which can additionally bear substituents and which, in its respective bonding state, has at least one free electron pair, A is an acceptor atom which can additionally bear substituents and which, in its respective bonding state, has at least one electron pair vacancy, where D and A are linked by a reversible coordinative bond in such a way that the donor group takes on a positive (partial) charge and the acceptor group takes on a negative (partial) charge, M represents a transition metal of transition group III, IV, V or VI of the Periodic Table of the Elements (Mendeleev) including the lanthanides and actinides, X is one anion equivalent and n is, depending on the charge of Me zero, one, two, three or four, with self-activation in which after opening of the D/A bond the acceptor atom A binds to an X ligand to form a zwitterionic metallocene complex structure generating a positive charge on the transition metal M and a negative charge on the acceptor atom A, where a further X ligand is H or substituted or unsubstituted C into whose bond to the transition metal M the olefin insertion for polymerization occurs and where preferably 2 X ligands are linked to one chelating ligand.

10. A reaction product of ionizing agents with a metallocene catalyst, said reaction product having the formula:

$$\left[ \begin{array}{c} \delta+D-CpI \\ \downarrow \\ \delta-A-CpII \end{array} \!\!\!\!\!\!\!\!\! MX_{n-1} \right]^{+} \text{Anion}^{-}, \text{ or} \qquad (XIa)$$

$$\left[ \begin{array}{c} \delta+D-CpI \\ \downarrow \\ \delta-A-CpII \end{array} \!\!\!\!\!\!\!\!\! MX_{n-1} \cdot Base \right]^{+} \text{Anion}^{-}, \qquad (XIb)$$

(XI), wherein

CpI and CpII are two identical or different carbanions having a cyclopentadienyl-containing structure in which from one to all H atoms can be replaced by identical or different radicals selected from the group consisting of linear or branched $C_1$–$C_{20}$-alkyl which may be monosubstituted to fully substituted by halogen, monosubstituted to trisubstituted by phenyl or monosubstituted to trisubstituted by vinyl; $C_6$–$C_{12}$-aryl; halogenoaryl having from 6 to 12 carbon atoms; and which may be monosubstituted or disubstituted by D and A, D is a donor atom which can additionally bear substituents and which, in its respective bonding state, has at least one free electron pair, A is an acceptor atom which can additionally bear substituents and which, in its respective bonding state, has at least one electron pair vacancy, Wherein D and A are linked by a reversible coordinative bond in such a way that the donor group takes on a positive charge and the acceptor groups takes on a negative charge, M represents a transition metal of transition group III, IV, V or VI of the Periodic Table of the Elements including the lanthanides and actinides, X is one anion equivalent and n is, depending on the charge of M, zero, one, two, three, or four, Base represents a Lewis base, and Anion represents the overall bulky anion which does not coordinate readily.

11. A reaction product according to claim 10, wherein said metallocene catalyst has the formula of:

$$\delta+D-CpI \atop \downarrow \atop \delta-A-CpII} \!\!\!\!\! MX_n \quad \longrightarrow \quad \underset{(Ib)}{D-CpI-CpI-A \atop MX_n} \qquad (I)$$

(Ia)                              (Ib)

12. A reaction product according to claim 10, wherein said ionizing agent comprises a cation which will irreversibly react with a ligand of one of the following formula (Ia) or (Ib):

$$\Delta+D-CpI \atop \downarrow \atop \Delta-A-CpII} \!\!\!\!\! MX_n \quad \longrightarrow \quad \underset{(Ib)}{D-CpI-CpI-A \atop MX_n}, \qquad (I)$$

(Ia)                              (Ib)

wherein

CpI and CpII are two identical or different carbanions having a cyclopentadienyl-containing structure in which from one to all H atoms can be replaced by identical or different radicals selected from the group consisting of linear or branched $C_1$–$C_{20}$-alkyl which may be monosubstituted to fully substituted by halogen, monosubstituted to trisubstituted by phenyl or monosubstituted to trisubstituted by vinyl; $C_6$–$C_{12}$-aryl; halogenoaryl having from 6 to 12 carbon atoms; and which may be monosubstituted or disubstituted by D and A, D is a donor atom which can additionally bear substituents and which, in its respective bonding state, has at least one free electron pair, A is an acceptor atom which can additionally bear substituents and which, in its respective bonding state, has at least one electron pair vacancy, Wherein D and A are linked by a reversible coordinative bond in such a way that the donor group takes on a positive charge and the acceptor groups takes on a negative charge, M represents a transition metal of transition group III, IV, V or VI of the Periodic Table of the Elements including the lanthanides and actinides, X is one anion equivalent and n is, depending on the charge of M, zero, one, two, three, or four.

13. A reaction product according to claim 12, wherein said ionizing agent is selected from the group consisting of Lewis acids and Bronsted acids.

14. A reaction product according to claim 12, wherein said ionizing agent comprises additionally, Lewis bases.

15. A rearrangement product according to claim 9, wherein said metallocene compound has the formula of:

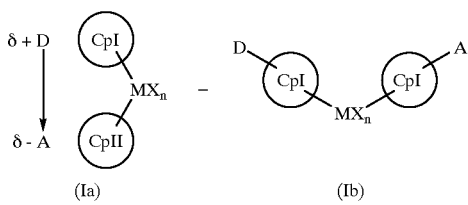

(Ia)      (Ib)

wherein

CpI and CpII are two identical or different carbanions having a cyclopentadienyl-containing structure in which from one to all H atoms can be replaced by identical or different radicals selected from the group consisting of linear or branched $C_1$–$C_{20}$-alkyl which may be monosubstituted to fully substituted by halogen, monosubstituted to trisubstituted by phenyl or monosubstituted to trisubstituted by vinyl; $C_6$–$C_{12}$-aryl; halogenoaryl having from 6 to 12 carbon atoms; and which may be monosubstituted or disubstituted by D and A, D is a donor atom which can additionally bear substituents and which, in its respective bonding state, has at least one free electron pair, A is an acceptor atom which can additionally bear substituents and which, in its respective bonding state, has at least one electron pair vacancy, Wherein D and A are linked by a reversible coordinative bond in such a way that the donor group takes on a positive charge and the acceptor groups takes on a negative charge, M represents a transition metal of transition group III, IV, V or VI of the Periodic Table of the Elements including the lanthanides and actinides, X is one anion equivalent and n is, depending on the charge of M, zero, one, two, three, or four.

16. A metallocene compound as claimed in claim 4, wherein the donor atoms D used are elements selected from the group consisting of N, P, O, and S.

17. A metallocene compound as claimed in claim 5, wherein the acceptor atoms A used are elements selected from the group consisting of B, Al, and Ga.

18. A metallocene compound as claimed in claim 7, wherein M represents Ti, Zr, Hf, V, Nb, or Ta.

\* \* \* \* \*

UNITED STATES PATENT AND TRADEMARK OFFICE
CERTIFICATE OF CORRECTION

PATENT NO. : 6,184,320 B1
DATED : February 6, 2001
INVENTOR(S) : Karl-Heinz Aleksander Ostoja Starzewski and Warren Mark Kelly It is certified that error appears in the above-identified patent and that said Letters Patent is hereby corrected as shown below:

Column 40,
Lines 25 through 34, the formula should appear as follows:

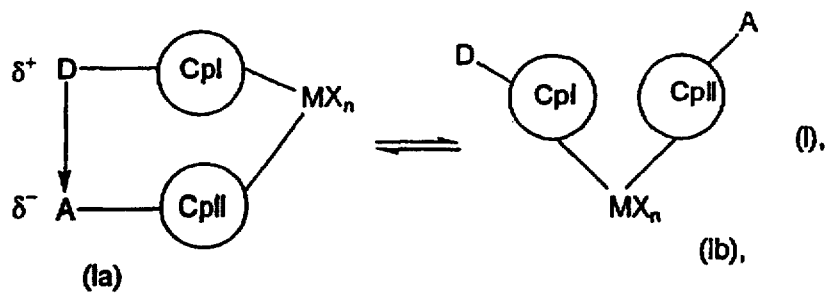

Column 42,
Lines 11 through 20, the formula should appear as follows:

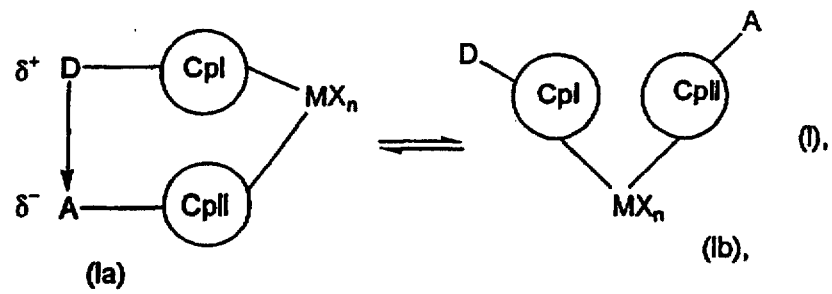

Lines 55 through 63, the formula should appear as follows:

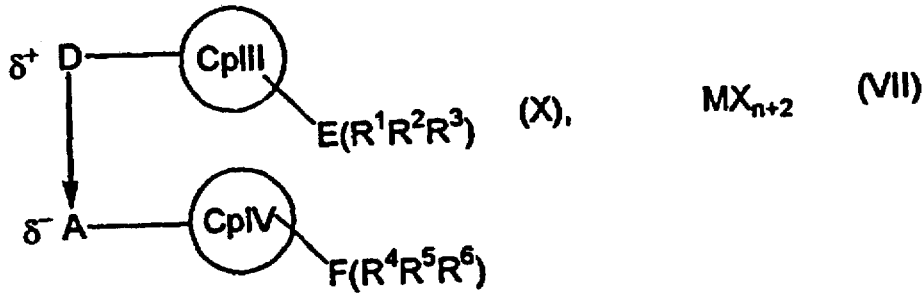

UNITED STATES PATENT AND TRADEMARK OFFICE
CERTIFICATE OF CORRECTION

PATENT NO. : 6,184,320 B1
DATED : February 6, 2001
INVENTOR(S) : Karl-Heinz Aleksander Ostoja Starzewski and Warren Mark Kelly It is certified that error appears in the above-identified patent and that said Letters Patent is hereby corrected as shown below:

Column 44,
Lines 37 through 45, the formula should appear as follows:

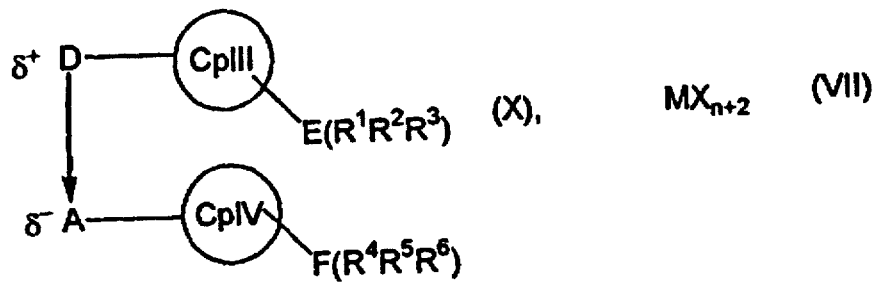

Column 46,
Lines 6 through 16, the formula should appear as follows:

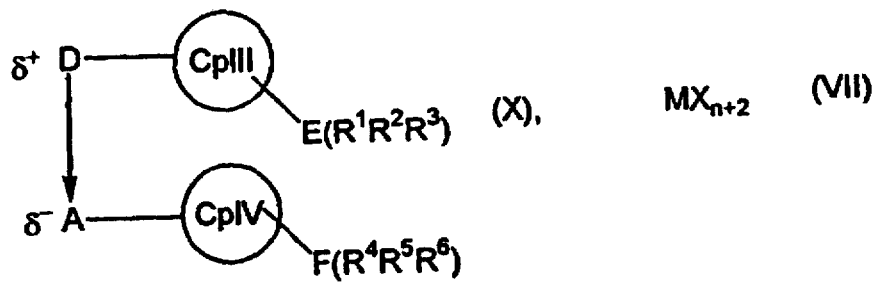

Lines 23 through 30, the formula should appear as follows:

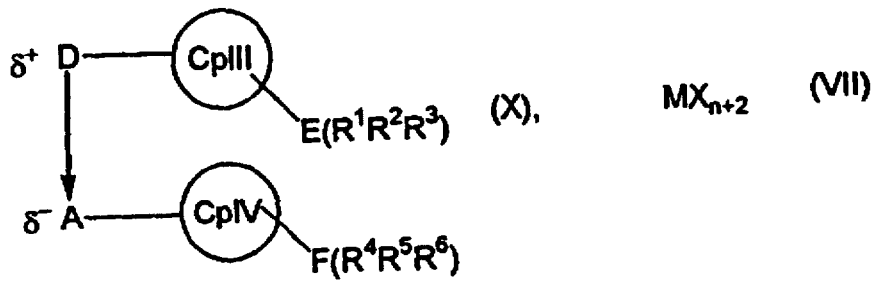

UNITED STATES PATENT AND TRADEMARK OFFICE
CERTIFICATE OF CORRECTION

PATENT NO. : 6,184,320 B1
DATED : February 6, 2001
INVENTOR(S) : Karl-Heinz Aleksander Ostoja Starzewski and Warren Mark Kelly It is certified that error appears in the above-identified patent and that said Letters Patent is hereby corrected as shown below:

Column 47,
Lines 1 through 10, the formula should appear as follows:

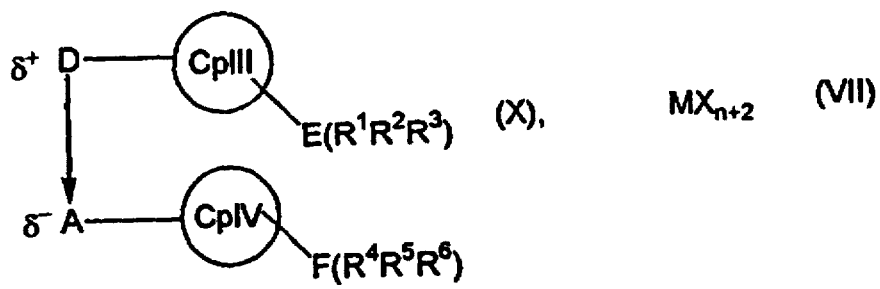

Signed and Sealed this

Twenty-third Day of April, 2002

Attest:

JAMES E. ROGAN
*Director of the United States Patent and Trademark Office*

*Attesting Officer*